United States Patent [19]

Rydel et al.

[11] Patent Number: 5,707,821

[45] Date of Patent: Jan. 13, 1998

[54] IDENTIFICATION OF PHOSPHOLIPASE A2 INHIBITORS IN Aβ PEPTIDE-MEDIATED NEURODEGENERATIVE DISEASE

[75] Inventors: Russell E. Rydel, Belmont; Michael S. Dappen, San Bruno, both of Calif.

[73] Assignee: Athena Neurosciences, Inc., San Francisco, Calif.

[21] Appl. No.: 476,464

[22] Filed: Jun. 7, 1995

[51] Int. Cl.$^6$ .............................. C12Q 1/34; A61K 00/00
[52] U.S. Cl. .................................. 435/18; 435/4; 514/12
[58] Field of Search ............................. 514/12; 435/18, 435/4

[56] References Cited

U.S. PATENT DOCUMENTS

| | | | |
|---|---|---|---|
| 5,137,873 | 8/1992 | Yankner | 514/15 |
| 5,281,626 | 1/1994 | Oinuma et al. | 514/603 |
| 5,328,842 | 7/1994 | Chiou et al. | 435/240.2 |
| 5,354,677 | 10/1994 | Knopf et al. | 435/198 |
| 5,453,443 | 9/1995 | Perrier et al. | 514/570 |
| 5,478,857 | 12/1995 | Clemens et al. | 514/381 |

FOREIGN PATENT DOCUMENTS 0 468 054 A1  1/1992  European Pat. Off. ...... C07C 311/46

OTHER PUBLICATIONS

Eikelenboom, P. et al. "Inflammatory mechanisms in Alzheimer's disease" Trends in Pharm. Sci. 15(12):447–450, (Dec. 1994).

Simmons, L. K. et al. "Secondary structure of amyloid beta peptide correlates with neurotoxic activity in vitro" Mol. Pharmacol. 45(3):373–379, (Mar. 1994).

Abdullah et al., "Human cytosolic phospholipase $A_2$ expressed in insect cells is extensively phosphorylated on Ser–505," Biochimica et Biophysica Acta, 1244:157–164 (1995).

Abdullah et al., "Synthesis and Preparation of an Affinity Chromatography Column for the Purification of Cytosolic Phospholipase $A_2$, " Bioorganic & Medicinal Chemistry Letters, 5(5):519–522 (1995).

Abdullah et al., "Purification of Baculovirus–Overexpressed Cytosolic Phospholipase $A^2$ Using a Single–Step Affinity Column Chromatography," Protein Expression and Purification, 6:291–297 (1995).

Ackermann et al., "Inhibition of Macrophage $Ca^{2+}$–independent Phospholipase $A_2$ by Bromoenol Lactone and Trifluoromethyl Ketones," J. Biol. Chem., 270(1):445–450 (1995).

Bartoli et al., "Tight Binding Inhibitors of 85–kDa Phospholipase $A_2$ but Not 14–kDa Phospholipase $A_2$ Inhibit Release of Free Arachidonate in Thrombin–stimulated Human Platelets," J. Biol. Chem., 269(22):15625–15630 (1994).

Currie et al., "Phosphorylation and activation of $Ca^{2+}$–sensitive cytosolic phospholipase $A_2$ in MCII mast cells mediated by high–affinity $F_c$ receptor for IgE," Biochem. J., 304:1–6 (1994).

Dennis, "Diversity of Group Types, Regulation, and Function of Phospholipase $A_2$," J. Biol. Chem., 269(18):13057–13060 (1994).

Glaser et al., "Phospholipase $A_2$ enzymes: regulation and inhibition," TiPS, 14:92–98 (1993).

Kramer, "Structure, Function and Regulation of Mammalian Phospholipases $A_2$," Advances in Second Messenger and Phosphoprotein Research, 28:81–89 (1993).

Lin et al., "cPLA$_2$ Is Phosphorylated and Activated by MAP Kinase," Cell, 72:269–278 (1993).

Mattson et al., "β–Amyloid precursor protein metabolites and loss of neuronal $Ca^{2+}$ homeostasis in Alzheimer's disease," TINS, 16(10):409–414 (1993).

Meda et al., "Activation of microglial cells by β–amyloid protein and interferon–τ," Nature, 374:647–650 (1995).

Oinuma et al., "Synthesis and Biological Evaluation of Substituted Benzenesulfonamides as Novel Potent Membrane–Bound Phospholipase $A_2$ Inhibitors," J. Med. Chem., 34:2260–2267 (1991).

Petit et al., "Isolation and Characterization of a Cytosolic Phospholipase $A_2$ from Bovine Adrenal Medulla," J. of Neurochem. 64:139–146 (1995).

Reynolds et al., "1–Hexadecyl–2–Arachidonoylthio–2–deoxy–sn–Glycero–3–Phosphorylcholine as a Substrate for Microtiterplate Assay of Human Cytosolic Phospolipase $A_2$," Anal. Biochem., 217:25–32 (1994).

Reynolds et al, "Assay Strategies and Methods for Phospholipases," Methods in Enzymology, 197:3–23 (1991).

Riendeau et al., "Arachidonyl Trifluoromethyl Ketone, a Potent Inhibitor of 85–kDa Phospholipase $A_2$, Blocks Production of Arachidonate and 12–Hydroxyeicosa–tetraenoic Acid by Calcium Ionophore–challenged Platelets," J. Biol. Chem., 269(22);15619–15624 (1994).

Roshak et al., "Suppression of Monocyte 85–kDa Phospholipase $A_2$ by Antisense and Effects on Endotoxin–induced Prostaglandin Biosynthesis," J. Biol. Chem., 269(42):25999–26005 (1994).

Street et al., "Slow– and Tight–Binding Inhibitors of the 85–kDa Human Phospholipase $A_2$," Biochem., 32:5935–5940 (1993).

Verity, "Mechanisms of Phospholipase $A_2$ Activation and Neuronal Injury," Annals NY Acad. Sci., 679:110–120 (1993).

Alberts, B. et al. Molecular Biology of the Cell, Second Edition. New York: Garland Publ. 1989, pp. 689–690 and 974.

Dumuis, A. et al. "Stimulation by glutamate receptors of arachidonic acid release depends on the Na+/Ca2+ exchanger in neuronal cells" Molec. Pharmacol. 43(6):976–981, abstract only, (Jun. 1993).

Primary Examiner—Robert A. Wax
Assistant Examiner—Kawai Lau
Attorney, Agent, or Firm—Jean Duvall, Esq.; John Storella, Esq.; Townsend and Townsend and Crew

[57] ABSTRACT

The invention provides methods and compositions for treating neurodegeneration in mammalian cells by administering a phospholipase A2 inhibitor.

7 Claims, 9 Drawing Sheets

AN20606

AN20628

U73122

AN22669

AN20602

U73343

QUINACRINE

AN22831

AN20606

AN20628

AN22757

MINOCYCLINE

MANOALIDE

AN22669

OLEOYLOXYETHYL PHOSPHOCHOLINE

P-BROMOPHENACYL BROMIDE 7,7-DIMETHYLEICOSADIENOIC ACID

DOXYCYCLINE

AN23019

IDENTIFICATION OF PHOSPHOLIPASE A2 INHIBITORS IN Aβ PEPTIDE-MEDIATED NEURODEGENERATIVE DISEASE

TECHNICAL FIELD

The invention relates to methods for inhibiting neurodegeneration in a mammalian neuronal cell population by administering a suitable inhibitor of phospholipase $A_2$ activity, typically an inhibitor of cPLA$_2$ (cytosolic phospholipase $A_2$); the invention also provides methods for identifying such suitable inhibitors of phospholipase activity, including selective inhibitors of cPLA$_2$, which have the property of inhibiting β-amyloid peptide-induced neuronal degeneration.

BACKGROUND

Alzheimer's disease (AD) is a progressive disease known generally as senile dementia. Broadly speaking the disease falls into two categories, namely late onset and early onset. Late onset, which occurs in old age (65+years), may be caused by the natural atrophy of the brain occurring at a faster rate and to a more severe degree than normal. Early onset AD is much more infrequent but shows a pathologically identical dementia with brain atrophy which develops well before the senile period, i.e., between the ages of 35 and 60.

Alzheimer's disease is characterized by the presence of numerous amyloid plaques and neurofibrillary tangles (highly insoluble protein aggregates) present in the brains of AD patients, particularly in those regions involved with memory and cognition. While in the past there was significant scientific debate over whether the plaques and tangles are a cause or are merely the result of AD, recent discoveries indicate that amyloid plaque is a causative precursor or factor. In particular, it has been discovered that the overproduction of β-amyloid peptide ("Aβ"), a major constituent of the amyloid plaque, can result from mutations in the gene encoding amyloid precursor protein.

One hypothesis regarding the pathogenesis of the disease is that deposition of Aβ peptide, which is the major macromolecular component of amyloid plaques, is the causative agent of the characteristic AD pathological changes leading to formation of neurofibrillary tangles, neuronal cell loss, vascular damage, and, ultimately, dementia (Hardy and Higgins (1992) *Science* 256: 184). Amyloid precursor protein (APP) is encoded by a single gene in humans. RNA transcripts of the APP gene are alternatively spliced to encode several APP protein isoforms; the predominant APP isoform in brain lacks a serine protease inhibitor domain that is present in other tissues. Aβ is a proteolytic cleavage product arising from the carboxy region of various APP isoforms, including the predominant APP isoform in the brain (U.S. Pat. No. 4,666,829; Glenner and Wong (1984) *Biochem. Biophys. Res. Commun.* 120: 1131; Kitaguchi et al. (1988) *Nature* 331: 530; Ponte et al., ibid., p.525; R. E. Tanzi, ibid., p.528; Kang and Muller-Hill (1990) *Biochem. Biophys. Res. Commun.* 166: 1192; Yoshioka et al. (1991) *Biochem. Biophys. Res. Commun.* 178.: 1141; Johnson et al. (1990) *Science* 248: 854; Neve et al. (1990) *Neuron* 5: 329). The accumulation of extracellular Aβ results in insoluble amyloid deposits and may be neurotoxic, leading to neuronal death and neurofibrillary tangle formation.

Moreover, Aβ peptide appears to be toxic to brain neurons, and neuronal cell death is associated with the disease (Schubert et al. (1995) *Proc. Natl. Acad. Sci. (USA)* 92: 1989; Lorenzo and Yankner (1994) *Proc. Natl. Acad. Sci. (USA)* 91: 12243; Yankner et al. (1990) *Science* 250: 279; Kowall et al. (1991) *Proc. Natl. Acad. Sci. (USA)* 88: 7247; and Pike et al. (1993) *J. Neurosci.* 13: 1676). Mattson et al. (1992) *J. Neurosci.* 12:376 and Mattson et al. (1993) *Trends in Neuroscience* 1.6: 409, report that Aβ and fragments thereof can destabilize calcium ($Ca^{+2}$) homeostasis in cultured human cortical neurons, and can render the neurons more susceptible to calcium ionophore-induced neurotoxicity. Meda et al. (1995) *Nature* 374:647 report that Aβ and IFN-γ activates cultured microglial cells, leading to neuronal cell injury in co-cultured neurons. Both Meda et al. (1995) op.cit and Schubert et al. (1995) op.cit report the likely involvement of reactive free radical species, such as reactive nitrogen intermediates and reactive oxygen species.

Reports show that soluble Aβ peptide is produced by healthy neuronal cells in culture media (Haass et al. (1992) *Nature* 359: 322) and is present in human and animal cerebrospinal fluid (Seubert et al. (1992) *Nature* 359: 325). Thus, the mere presence of soluble Aβ peptide may not be sufficient for explaining the onset and progression of AD. However, aggregation and formation of insoluble complexes of Aβ have been implicated as having enhanced neurotoxicity to cultured neuronal cells.

To date, the exact molecular mechanisms which result in the characteristic pathology and neuronal deficits of Alzheimer's disease have not been described in the art. The development of experimental models of Alzheimer's disease that can be used to define further the underlying biochemical events involved in AD pathogenesis would be highly desirable. Such models could presumably be employed, in one application, to screen for agents that alter the degenerative course of Alzheimer's disease. For example, a model system of the biochemical events which contribute to the pathology of Alzheimer's disease could be used to screen for drugs or therapeutic regimens that reverse, arrest, or slow the pathogenesis and progression of AD. Presumably, such models could be employed to develop pharmaceuticals that are effective in preventing, arresting, or reversing AD.

Currently, there are no human pharmaceuticals which are known to be effective in inhibiting the development or progression of the degenerative CNS neuropathology of Alzheimer's Disease. U.S. Pat. No. 5,192,753 report that certain non-steroidal anti-inflammatory drugs useful in treating rheumatoid arthritis (e.g., indomethacin) are allegedly useful in reducing symptomatic progression in a selected group of five AD patients, but no effects on neuropathological progression were noted and the sample size and experimental methodology employed were insufficient to conclusively demonstrate efficacy. U.S. Pat. No. 5,137,873 disclose the use of tachykinin agonists to treat AD, although this approach has not proven successful in producing substantial amelioration of the progression of AD, and significantly more effective therapeutic agents are desired in the art.

There is a need in the art for pharmaceuticals which have therapeutic use to treat or prevent Alzheimer's Disease and Aβ-related neurodegenerative diseases which have similar pathogenic mechanisms. A more thorough understanding of the molecular events underlying the development and progression of such Aβ related neurodegenerative diseases would facilitate development of such pharmaceuticals. Identification of critical biochemical events involved in these Aβ-related neurodegenerative diseases can provide a basis for development of methods and model systems for screening compound banks to identify such pharmaceuticals, as well as providing a basis for the design of therapeutic methods and treatment modalities for Alzheimer's disease.

It would be desirable to have methods and model systems for screening test compounds for the ability to inhibit or prevent neuronal toxicity produced by neurotoxic forms of a pathogenic Aβ peptide. In particular, it would be desirable to base such methods and systems on metabolic pathways and/or signal transduction pathways which have been found to be involved in such pathogenesis, where the test compound would be able to interrupt or interfere with the metabolic pathway or signal transduction pathway which leads to damage of neuronal and/or glial cells in the presence of pathogenic forms of Aβ. Such methods and systems should provide rapid, economical, and suitable means for screening large numbers of test compounds.

Based on the foregoing, it is clear that a need exists for identification of metabolic pathways and/or signal transduction pathways which have been found to be involved in the pathogenesis of Aβ-mediated neurodegenerative diseases, and the development of methods of treatment and pharmaceutical screening assays based on the identification of these pathways. The present invention fulfills these and other needs in the art.

The references discussed herein are provided solely for their disclosure prior to the filing date of the present application. Nothing herein is to be construed as an admission that the inventors are not entitled to antedate such disclosure by virtue of prior invention.

SUMMARY OF THE INVENTION

A basis of the present invention is the unexpected finding that Aβ-mediated neuronal cell degeneration is mediated by a biochemical cascade which requires activity of phospholipase $A_2$, ("$PLA_2$"), an enzyme which catalyzes the hydrolysis of the fatty acid ester bond at the sn-2 position of membrane phospholipids to produce arachidonic acid and its metabolites, and in the case of one cytosolic form of $PLA_2$, $cPLA_2$, also produces lysophospholipids. Agents which selectively block $PLA_2$ activity in neurons and/or glial cells and/or astrocytes or monocytes can be used to inhibit Aβ-mediated neuronal degeneration, such as that which results from exposure of such cells to pathogenic forms of Aβ as occurs in Alzheimer's Disease and related Aβ-induced neurodegenerative conditions. These selective $PLA_2$-blocking agents can be used to inhibit neuronal degeneration resulting from Aβ toxicity.

In one aspect, the invention provides a method for identifying active agents which significantly inhibit neuronal degeneration induced by pathogenic Aβ peptides or their analogs, either directly or via their effects on secondary cell types such as microglial cells, astrocytes, macrophages, or other non-neuronal cells which interact with central nervous system neurons and which can manifest Aβ toxicity. The method comprises administering an agent to a cell population comprising neurons, wherein said cell population is exposed to an amount of pathogenic Aβ capable of inducing neuronal degeneration in the cell population, and determining whether the presence of said agent produces inhibition of $PLA_2$ activity and, typically, also produces a detectable reduction in the amount and/or rate of neuronal degeneration in the cell population; if said agent produces $PLA_2$ inhibition in neurons and/or inhibits neuronal degeneration, the agent is thereby identified as an active agent. Preferably, the method is used to demonstrate that the active agent inhibits $PLA_2$ activity and also inhibits Aβ-mediated neuronal degeneration.

In a variation of the method, the agent is initially selected from a bank (or library) of compounds on the basis of the agent's capacity or selectivity for inhibiting $PLA_2$ in vitro, such as by its ability to inhibit $PLA_2$ enzymatic activity in an in vitro assay employing a predetermined amount of a standardized preparation of $PLA_2$; an agent which is thus initially selected is administered to a cell population comprising neurons, wherein said cell population is exposed to an amount of pathogenic Aβ capable of inducing neuronal degeneration in the cell population, and the capacity of said agent to produce a detectable reduction in the amount and/or rate of neuronal degeneration in the cell population is determined, with agents capable of reducing Aβ-induced neuronal degeneration being thereby identified as active agents. In this variation, the capacity of the agent to selectively or specifically inhibit $PLA_2$ in a cultured cell population comprising neurons can optionally be determined.

In an aspect, the invention also provides a method for identifying an active agent which significantly inhibits neuronal degeneration in a transgenic animal model of Alzheimer's Disease; such active agents can be sold commercially as reagents to control the disease phenotype of such transgenic animals for any purpose desired by an end-user of such animals, and can serve as candidate pharmaceuticals for therapy of Aβ-mediated neurodegenerative disease, among other uses. The method comprises initially selecting an $PLA_2$-inhibiting agent from a bank (or library) of compounds on the basis of: (1) the agent's capacity, selectivity, or specificity for inhibiting $PLA_2$ in vitro, such as by its ability to inhibit $PLA_2$ enzymatic activity in an in vitro assay employing a predetermined amount of a standardized preparation of $PLA_2$, and/or (2) the capacity of the agent to selectively inhibit $PLA_2$ in a cultured cell population comprising neurons; and administering the selected agent to a transgenic animal capable of developing detectable pathology characteristic of Alzheimer's Disease, and determining whether administration of the selected agent inhibits or retards development of said detectable pathology as compared to a substantially identical control transgenic animal which lacks the agent; an agent which retards or inhibits development of AD pathology is thereby identified as an active agent.

In an aspect, the invention provides a method for reducing or retarding neurodegeneration in a cell population comprising neurons and exposed to an amount of pathogenic Aβ sufficient to produce neurodegeneration; said method comprising administering an efficacious dose of a $PLA_2$ inhibitor predetermined to retard or inhibit neuronal degeneration. In one embodiment, the cell population may reside in the central nervous system of a mammal and the $PLA_2$ inhibitor is administered in vivo. The invention also provides the use of a $PLA_2$ inhibitor to treat Aβ-mediated neurodegenerative disease pathology in a mammal.

In an aspect, the invention provides a method for retarding or inhibiting Aβ-induced neurodegeneration in a cell population comprising neurons and exposed to an amount of pathogenic Aβ sufficient to produce neurodegeneration; said method comprising administering to the cell population an efficacious dose of an antisense polynucleotide capable of inhibiting expression of $PLA_2$, typically by reducing transcription and/or translation of the $PLA_2$ gene sequences. In one embodiment, the cell population may reside in the central nervous system of a mammal and the $PLA_2$ inhibitor is administered in vivo. The invention also provides the use of a $PLA_2$ antisense polynucleotide to treat Aβ-mediated neurodegenerative disease pathology in a mammal. In an embodiment, the antisense polynucleotide is produced by transcription of a transgene or gene therapy vector incorporated into a cell or animal; alternatively, antisense oligonucleotides can be administered in soluble form, formulated in liposomes, or by other suitable delivery format.

In an aspect, the invention provides a transgenic animal, such as a transgenic mouse, which harbors a transgene encoding a functional $PLA_2$ enzyme and capable of transcription and translation in neuronal and/or astrocytes and/or microglial cells in vivo. Typically, the transgene comprises a gene encoding a human $PLA_2$ enzyme operably linked to a transcriptional regulatory sequence which is transcriptionally active in neural cell types, and is preferably inducible. In one variation, the 5' flanking portion of the murine or human $PLA_2$ or APP gene, including the promoter (and frequently including an upstream portion and/or intronic portion(s) often having enhancer activity) and sufficient to drive transcription of linked sequences in the brain of a transgenic animal, serves as the transcriptional regulatory sequence of the $PLA_2$-encoding transgene. Such transgenic animals can overexpress $PLA_2$, either constitutively or inducibly, and can serve as models of accelerated $A\beta$-mediated neurodegenerative disease; such animals can be sold for toxicological and pharmaceutical applications for evaluation of compounds or agents (physical or chemical) which modulate $PLA_2$-mediated $A\beta$ neurodegeneration.

The invention also provides, in an aspect, a knockout animal comprising a genome having a homozygous pair of functionally disrupted endogenous $PLA_2$ alleles, such that substantially no endogenous $PLA_2$ is expressed. In a variation, the knockout animal genome also comprises a transgene encoding a heterologous $PLA_2$ enzyme (e.g., a $PLA_2$ knockout mouse having a transgene encoding human $PLA_2$), which is expressed under the control of an operably linked transcriptional regulatory sequence, such as the naturally occurring mouse $PLA_2$ promoter and 5' flanking sequence.

In a variation, the invention provides a knockout mouse having a genome comprising a homologous pair of functionally inactivated mouse $PLA_2$ alleles and a transgene encoding and expressing a pathogenic human APP gene product, such as a human Swedish mutation APP transgene, human APP717 mutant APP transgene, or the like. Optionally, the mouse genome may further comprise a transgene encoding a mammalian $PLA_2$ which is transcribed under the control of a transcriptional regulatory sequence which is inducible or repressible in neuronal cells.

In an aspect of the invention, an agent is selected from a compound library on the basis of its detectable inhibition of $PLA_2$ activity in an in vitro $PLA_2$ enzyme assay and/or in a cell culture $PLA_2$ assay system; the agent is administered to a transgenic animal of the invention which is expressing $PLA_2$ in neuronal tissue to thereby generate a treated transgenic animal refractory to AD-type neurodegenerative pathology and/or evaluate the suitability of the selected agent for in vivo administration.

Also provided by the invention is a method for inhibition of $A\beta$-induced neuronal cell death in a cell population comprising mammalian glial cells and neuronal cells. The method comprises delivering an effective dosage of an $PLA_2$ inhibitor to a cell population comprising $A\beta$-mediated neurotoxicity. Typically, the cell population is a co-cultured cell population of human or rat hippocampal or cortical neurons and human microglia and/or human astrocytes and/or monocytes. In some variations, transgenic animals may serve as the source of the glial and/or neuronal cells. The cell population also may reside in a mammalian central nervous system in vivo.

Other aspects of the invention will be evident by reference to the specification and examples provided herein.

All publications and patent applications herein are incorporated by reference to the same extent as if each individual publication or patent application was specifically and individually indicated to be incorporated by reference.

DEFINITIONS

Figure 1A:
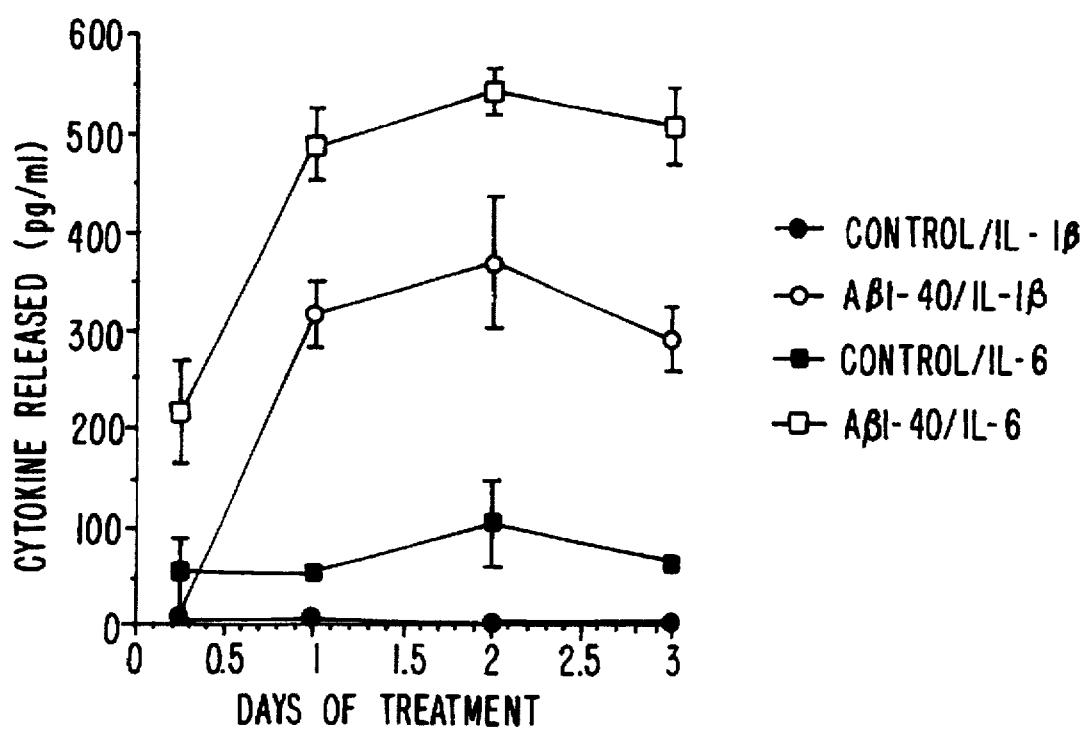
FIG. 1 (panels A and B) shows the expression of cytokine induced by $A\beta$ peptide in human microglial cells. Panel A shows IL-1$\beta$ and IL-6 cytokine release. Panel B shows TNF$\alpha$ release.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of the present invention, the following terms are defined below.

The term "$A\beta$ peptide-mediated neurodegeneration" as used herein refers to degeneration of neuronal cells (e.g., cortical or hippocampal neurons, primary neuron cultures, neuronal cell lines) which is causally linked to accumulation of neurotoxic $A\beta$ peptide; such toxicity may be manifested in the neuronal cells by direct interaction with toxic $A\beta$ peptide or via indirect effects resulting from interaction of $A\beta$ peptide with neuronal-associated cells (e.g., astrocytes, astrocytoma cells, microglial cells, monocytes, etc.). Such indirect effects may involve nitric oxide formation, excitatory amino acid mimetics, and/or cytokine production by the non-neuronal cells, whereby such compounds produce neuronal cell damage. $A\beta$ peptide-mediated neurodegenerative diseases are exemplified, but not limited to, Alzheimer's Disease. Some neuropathologies may be causally associated with aberrant forms or amounts of other fragments or isoforms of the APP gene besides $A\beta$; these neuropathologies are also defined herein as $A\beta$ peptide-mediated neurodegenerative diseases for purposes of this specification.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring. As used herein, laboratory strains of rodents which may have been selectively bred according to classical genetics are considered naturally-occurring animals.

The term "active agent" is used herein to refer to an agent which is identified by one or more screening method(s) of the invention as an agent which inhibits $PLA_2$ activity and retards or reduces Aβ-induced neurodegeneration. Active agents can be sold as commercial reagents for standardizing toxicological or pharmaceutical evaluations which employ neuron cultures or transgenic animals which exhibit Aβ-mediated neurodegenerative pathology. Some active agents will have therapeutic potential as drugs for human use, such as being administered to AD patients or individuals ascertained to be predisposed to developing AD or AD-type pathology (e.g., Down's Syndrome patients or familial AD). Active agents are often small (<3,000 Daltons) organic molecules, but may be macromolecules (e.g., polypeptides, polynucleotides, etc.), inorganic compounds, including metal salts. A selective inhibitor of $PLA_2$ produces a preferential inhibition of $PLA_2$ as compared to inhibition of other mammalian phospholipases; such that the concentration required to produce inhibition of 50% of $PLA_2$ catalytic activity is at least one order of magnitude lower than the concentration required to produce inhibition of 50% of the catalytic activity of phospholipases other than $PLA_2$. A selective inhibitor of $cPLA_2$ produces a preferential inhibition of $cPLA_2$ as compared to inhibition of other mammalian $PLA_2$ enzymes.

The term "agent" is used herein to denote a chemical compound, a mixture of chemical compounds, a biological macromolecule, or an extract made from biological materials such as bacteria, plants, fungi, or animal (particularly mammalian) cells or tissues. Agents are evaluated for potential activity as active agents by inclusion in screening assays described hereinbelow. Agents may be selected from a combinatorial compound library for the capacity to interact with and/or inhibit $PLA_2$. The agent library may be naive or may be composed of structural analogs of known $PLA_2$ inhibitors, or a combination of both. Example agents of a type known to inhibit $PLA_2$ would include arachidonic acid derivatives and analogs (e.g., arachidonyl trifluoromethyl ketone), benzenesulfonamides, aminosteroids, bromoenol lactone, manoalide, p-bromophenacyl bromide, minocycline, doxycycline, 7,7,-dimethyl-5,8-eicosadienoic acid, quinacrine, and the like, among others known in the art.

The term "PLA2" as used herein refers to a naturally-occurring mammalian $PLA_2$ polypeptide having enzymatic activity. A paradigmatic $PLA_2$ can be considered to be human $cPLA_2$ substantially equivalent to that such as that described in U.S. Pat. No. 5,354,677 and 5,328,842; Clark et al. (1991) *Cell* 65: 1043, and Sharp et al. (1991) *J. Biol. Chem.* 266: 14850, each incorporated herein by reference, or the cognate $cPLA_2$ enzyme in a non-human mammalian species. $PLA_2$ activity is present in a variety of cytosolic and extracellular $PLA_2$ polypeptide species. A preferred $PLA_2$ polypeptide of the invention is a cytosolic $PLA_2$, such as $cPLA_2$, and typically a calcium-activable $cPLA_2$ which is activated (exhibits enhanced catalytic activity) by the presence of calcium ions ($Ca^{+2}$)

The term "pathogenic Aβ peptide" refers to polypeptides comprising a peptide sequence encoded by the APP gene which have the property of producing neurotoxicity on neuronal cell cultures and/or primary neurons, typically in the presence of microglial cells and/or astrocytic cells and/or monocytes, or directly; generally a pathogenic Aβ peptide comprises at least residues 25–35 of the amyloid β protein, and often consists of residues 1–40 or 1–42 of the amyloid β peptide. Generally, polypeptide sequences encoded by the APP gene which are flanking the 1–42 Aβ sequence (SEQ ID NO:1)

-DAEFRHDSGYEVHHQKLVFFAEDVGSNK-GAIIGLMVGGVVIA-(SEQ ID NO:1)

are absent. Preferred Aβ peptides are:

Aβ1–40, amino acid sequence (SEQ ID NO:2)=

DAEFRHDSGYEVHHQKLVFFAEDVGSNKGAIIGLMVGGVV (SEQ ID NO:2)

Aβ1–42, amino acid sequence (SEQ ID NO:1)=

DAEFRHDSGYEVHHQKLVFFAEDVGSNK-GAIIGLMVGGVVIA (SEQ ID NO:1)

Neurotoxicity of any Aβ peptide can be determined by assay for neuronal cell viability according to the methods of the invention and according to methods known in the art. Typically, neurotoxicity of a pathogenic Aβ peptide will be dose-dependent. For example, dosages of 1–100 μM can be used. Furthermore, aggregation state of the Aβ peptide is believed to affect toxicity.

The term "cognate" as used herein refers to a gene sequence that is evolutionarily and functionally related between species. For example but not limitation, in the human genome, the human CD4 gene is the cognate gene to the mouse CD4 gene, since the sequences and structures of these two genes indicate that they are the most highly homologous match between the two species and both genes encode a protein which functions similarly (e.g., in signaling T cell activation through MHC class II-restricted antigen recognition).

As used herein, the term "xenogenic" is defined in relation to a recipient mammalian host cell or nonhuman animal and means that an amino acid sequence or polynucleotide sequence is not encoded by or present in, respectively, the naturally-occurring genome of the recipient mammalian host cell or nonhuman animal. Xenogenic DNA sequences are foreign DNA sequences; for example, a human $cPLA_2$ gene is xenogenic with respect to murine ES cells; also, for illustration, a human cystic fibrosis-associated CFTR allele is xenogenic with respect to a human cell line that is homozygous for wild-type (normal) CFTR alleles. Thus, a cloned murine nucleic acid sequence that has been mutated (e.g., by site directed mutagenesis) is xenogenic with respect to the murine genome from which the sequence was originally derived, if the mutated sequence does not naturally occur in the murine genome.

As used herein, a "heterologous gene" or "heterologous polynucleotide sequence" is defined in relation to the transgenic nonhuman organism producing such a gene product. A heterologous polypeptide, also referred to as a xenogeneic polypeptide, is defined as a polypeptide having an amino acid sequence or an encoding DNA sequence corresponding to that of a cognate gene found in an organism not consisting of the transgenic nonhuman animal. Thus, a transgenic mouse harboring a human $cPLA_2$ gene can be described as harboring a heterologous $cPLA_2$ gene. A transgene containing various gene segments encoding a heterologous protein sequence may be readily identified, e.g. by hybridization or DNA sequencing, as being from a species of organism other than the transgenic animal. For example, expression of human $cPLA_2$ amino acid sequences may be detected in the transgenic nonhuman animals of the invention with antibodies specific for human $cPLA_2$ epitopes encoded by human $cPLA_2$ gene segments. A cognate heterologous gene refers to a corresponding gene from another species; thus, if murine $cPLA_2$ is the reference, human $cPLA_2$ is a cognate heterologous gene (as is porcine, ovine, or rat $cPLA_2$, along with $cPLA_2$ genes from other species). A mutated endogenous gene sequence can be referred to as a heterologous gene; for example, a transgene encoding a murine $cPLA_2$ comprising a mutation (which is not known in naturally-occurring murine genomes) is a heterologous transgene with respect to murine and non-murine species.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing, such as a polynucleotide sequence of a mammalian $PLA_2$ gene, or may comprise a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (1981) *Adv. Appl. Math.* 2: 482, by the homology alignment algorithm of Needleman and Wunsch (1970) *J. Mol. Biol.* 48: 443, by the search for similarity method of Pearson and Lipman (1988) *Proc. Natl. Acad. Sci. (U.S.A.)* 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25–50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence.

As used herein, the term "transcriptional unit" or "transcriptional complex" refers to a polynucleotide sequence that comprises a structural gene (exons), a cis-acting linked promoter and other cis-acting sequences necessary for efficient transcription of the structural sequences, distal regulatory elements necessary for appropriate tissue-specific and developmental transcription of the structural sequences, and additional cis sequences important for efficient transcription and translation (e.g., polyadenylation site, mRNA stability controlling sequences).

As used herein, "linked" means in polynucleotide linkage (i.e., phosphodiester linkage). "Unlinked" means not linked to another polynucleotide sequence; hence, two sequences are unlinked if each sequence has a free 5'terminus and a free 3'terminus.

As used herein, the term "operably linked" refers to a linkage of polynucleotide elements in a functional relationship. A nucleic acid is "operably linked" when it is placed into a functional relationship with another nucleic acid sequence. For instance, a promoter or enhancer is operably linked to a coding sequence if it affects the transcription of the coding sequence. Operably linked means that the DNA sequences being linked are typically contiguous and, where necessary to join two protein coding regions, contiguous and in reading frame.

As used herein, the term "targeting construct" refers to a polynucleotide which comprises: (1) at least one homology region having a sequence that is substantially identical to or substantially complementary to a sequence present in a host cell endogenous gene locus, and (2) a targeting region which becomes integrated into an host cell endogenous gene locus by homologous recombination between a targeting construct homology region and said endogenous gene locus sequence. If the targeting construct is a "hit-and-run" or "in-and-out" type construct (Valancius and Smithies (1991) *Mol. Cell. Biol.* 11: 1402; Donehower et al. (1992) *Nature* 356: 215; (1991) *J. NIH Res.* 3: 59; Hasty et al. (1991) *Nature* 350; 243, which are incorporated herein by reference), the targeting region is only transiently incorporated into the endogenous gene locus and is eliminated from the host genome by selection. A targeting region may comprise a sequence that is substantially homologous to an endogenous gene sequence and/or may comprise a nonhomologous sequence, such as a selectable marker (e.g., neo, tk, gpt). The term "targeting construct" does not necessarily indicate that the polynucleotide comprises a gene which becomes integrated into the host genome, nor does it necessarily indicate that the polynucleotide comprises a complete structural gene sequence. As used in the art, the term "targeting construct" is synonymous with the term "targeting transgene" as used herein.

The terms "homology region" and "homology clamp" as used herein refer to a segment (i.e., a portion) of a targeting construct having a sequence that substantially corresponds to, or is substantially complementary to, a predetermined endogenous gene sequence, which can include sequences flanking said gene. A homology region is generally at least about 100 nucleotides long, preferably at least about 250 to 500 nucleotides long, typically at least about 1000 nucleotides long or longer. Although there is no demonstrated theoretical minimum length for a homology clamp to mediate homologous recombination, it is believed that homologous recombination efficiency generally increases with the length of the homology clamp. Similarly, the recombination efficiency increases with the degree of sequence homology between a targeting construct homology region and the endogenous target sequence, with optimal recombination efficiency occurring when a homology clamp is isogenic with the endogenous target sequence.

The terms "functional disruption" or "functionally disrupted" as used herein means that a gene locus comprises at least one mutation or structural alteration such that the functionally disrupted gene is incapable of directing the efficient expression of functional gene product. The invention encompasses knockout animals, such as mice, which are homozygous for a functionally disrupted $PLA_2$ gene, typically a $cPLA_2$ gene. For example but not limitation, an endogenous $cPLA_2$ gene that has a neo gene cassette integrated into an exon (e.g., the second exon) of a $cPLA_2$ gene, is not capable of encoding a functional protein (isoform) that comprises the inactivated exon, and is therefore a functionally disrupted $cPLA_2$ gene locus. Also for example, a targeted mutation in the exons of an endogenous $cPLA_2$ gene may result in a mutated endogenous gene that can express a truncated $PLA_2$ protein. Functional disruption can include the complete substitution of a heterologous $cPLA_2$ gene locus in place of an endogenous $cPLA_2$ locus, so that, for example, a targeting transgene that replaces the entire mouse $cPLA_2$ locus with a human $cPLA_2$ allele, which may be functional in the mouse, is said to have functionally disrupted the endogenous murine $cPLA_2$ locus by displacing it. Preferably, at least one exon which is incorporated into the mRNAs encoding most or all of the $cPLA_2$ isoforms are functionally disrupted. Deletion or interruption of essential transcriptional regulatory elements, polyadenylation signal (s), splicing site sequences will also yield a functionally disrupted gene. Functional disruption of an endogenous $cPLA_2$ gene, may also be produced by other methods (e.g., antisense polynucleotide gene suppression). The term "structurally disrupted" refers to a targeted gene wherein at least one structural (i.e., exon) sequence has been altered by homologous gene targeting (e.g., by insertion, deletion, point mutation(s), and/or rearrangement). Typically, $cPLA_2$ alleles that are structurally disrupted are consequently functionally disrupted, however $cPLA_2$ alleles may also be functionally disrupted without concomitantly being structurally disrupted, i.e., by targeted alteration of a non-exon sequence such as ablation of a promoter. An allele comprising a targeted alteration that interferes with the efficient expression of a functional gene product from the allele is referred to in the art as a "null allele" or "knockout allele".

DETAILED DESCRIPTION

Overview

A basis of the present invention is the unexpected finding that Aβ-mediated neuronal cell degeneration is mediated by a biochemical cascade which requires $PLA_2$ activity, an enzyme which catalyzes the hydrolysis of the fatty acid ester bond at the sn-2 position of membrane phospholipids to produce arachidonic acid and its metabolites, and in the case of the cytosolic form, $cPLA_2$, also produces lysophospholipids. Agents which selectively block $PLA_2$ activity in neurons (such as neuronal cell lines and cultured neurons) and/or glial cells (including glial cell lines) can be used to inhibit Aβ-mediated neuronal degeneration, such as that which results from exposure of such cells to pathogenic forms of Aβ as occurs in Alzheimer's Disease and related neurodegenerative conditions. These selective $PLA_2$-blocking agents can be used to inhibit and/or retard Aβ-mediated neuronal degeneration.

Cellular models of Alzheimer's Disease (AD) neuropathology are based on the ability of the Alzheimer's Disease-associated Aβ peptide to induce biological changes (e.g., microglia and astrocyte activation, monocyte activity, neuronal degeneration) in cultured human and rodent cell populations (neurons, neuronal cell lines, microglia, microglial cell lines, astrocytes, astrocytoma cells and cell lines, monocytes and monocytic cell lines) and neuronal and glial cell lines, wherein the biological changes mimic the neuropathological changes associated with Alzheimer's Disease.

A basis of the invention is the unexpected observation that several structurally dissimilar inhibitors of $PLA_2$ were capable of inhibiting Aβ-mediated microglial activation and Aβ-mediated neuronal degeneration in such cellular models of AD. Based on this observation and others made by Applicants, it is believed that $PLA_2$ activity is an essential component of Aβ-mediated neuropathological changes, such as those which occur in AD and Down's Syndrome. Active agents which inhibit $PLA_2$ activity are expected to inhibit Aβ-mediated neuropathological changes.

Phospholipase $A_2$

Phospholipases $A_2$ ($PLA_2$s; EC 3.1.1.4) are enzymes that hydrolyze the 2-acyl ester bond of phosphoglycerides generating free fatty acids and lysophospholipids (for review, see, Kramer, R. M. (1993) *Advances in Second Messenger and Phosphoprotein Research* 28: 81; Glaser et al. (1993) *TiPS* 14: 92; Dennis EA (1994) *J. Biol. Chem.* 269: 13057). $PLA_2$s are a diverse class of enzymes with regard to function, localization, regulation, mechanism, sequence, structure, and role of divalent metal ions.

In general, $PLA_2$ enzymes catalyze the hydrolysis of the fatty acid ester bond at the sn-2 position of membrane phospholipids to produce arachidonic acid and its metabolites. A variety of polypeptide species can exhibit PLA2 activity; for purposes of this specification, these polypeptides are considered $PLA_2$ isozymes.

Group I, II, and III $PLA_2$s are extracellular enzymes of approximately 14–18 kD in humans, and are designated $sPLA_2$s, in recognition of their secretion. $sPLA_2$s are found in many extracellular fluids and have a broad substrate specificity for many types of phospholipids.

Group IV $PLA_2$ is a cytosolic enzyme of approximately 85 kD (based on deduced cDNA coding sequence) to 110 kD (based on SDS-PAGE of purified protein), and is designated $cPLA_2$ to indicate its cytosolic location. Unlike $sPLA_2$s, the $cPLA_2$ enzyme exhibits preferential catalysis of phospholipids which contain arachidonic acid, and is most likely the enzyme responsible for arachidonic acid release which is the rate-limiting step for subsequent eicosanoid biosynthesis of pro-inflammatory lipid mediators (prostaglandins, leukotrienes, lipoxins, and platelet-activating factor: "PAF").

Other PLA$_2$ activities, both cytosolic and extracellular, are less well-characterized with regard to macromolecular identification and polypeptide sequences.

cPLA$_2$ is present in the cytosol of a variety of species and cell types, including human U937 cells (monocytes), platelets, kidney, and macrophages, among others, and is implicated in controlling arachidonic acid metabolism and eicosanoid production.

Human cPLA$_2$ has been cloned as a cDNA isolated from mRNA of a human monocytic cell line (U.S. Pat. Nos. 5,354,677 and 5,328,842; Sharp et al. (1991) op.cit; Clark et al. (1991) op.cit) and the mRNA encodes a protein of 749 amino acids which has little detectable homology with the secreted sPLA$_2$s or any other protein in known sequence databases. The cPLA$_2$ cDNA identifies a single copy gene in the human genome, with no detectable closely related genes based on Southern blotting experiments.

cPLA$_2$ contains an amino-terminal domain which binds calcium and similar divalent cations, and cPLA$_2$ binds to membrane vesicles at submicromolar concentrations of Ca$^{+2}$ in a calcium-dependent fashion. cPLA$_2$ can translocate to membranes when activated in the presence of calcium. Presumably, cPLA$_2$ associates with membrane components in vivo under suitable calcium concentrations. Agents that stimulate the release of arachidonic acid (ATP, thrombin, phorbol ester, calcium ionophore) can cause increased serine phosphorylation of cPLA$_2$ which increases the enzymatic activity of cPLA$_2$ (Lin et al. (1993) *Cell* 72: 269). Phosphorylation is believed to contribute to the control of cPLA$_2$ activity in vivo (Lin et al. (1992) *Proc. Natl. Acad. Sci. (USA)* 89: 6147; Lin et al. (1993) *Cell* 72: 269; Qiu et al. (1993) *J. Biol. Chem.* 268: 24506; Kramer et al. (1993) *J. Biol. Chem.* 268: 26796).

Antibodies have been raised against human cPLA$_2$ and crossreact with cPLA$_2$ from a variety of animals, indicating conservation of structure between species. Anti-cPLA$_2$ antibodies identify the presence of cPLA$_2$ in lung, brain, testis, kidney, spleen, liver, and heart, although the precise role of cPLA$_2$ in the metabolism of each of these tissues is not known (see, EP 0501779).

The art generally recognizes the physiologic role of cPLA$_2$ to be in the mediation of inflammation via its role in arachidonic acid metabolism and lipid/lipoprotein metabolism, such as cell membrane homeostasis. Roshak et al. (1994) *J. Biol. Chem.* 269: 25999 used antisense oligonucleotides complementary to the cPLA$_2$ mRNA to inhibit prostaglandin production in LPS-induced monocytes, indicating a potential role for cPLA$_2$ in generating inflammatory regulators in monocytes. Verity MA (1993) *Ann. N.Y. Acad. Sci.* 679:110 speculates that "abusive activation" of PLA$_2$ via uncontrolled Ca$^{+2}$ influx might produce irreversible cell injury of neurons via extensive localized lipid peroxidation and subsequent membrane disintegration. U.S. Pat. Nos. 5,354,677 and 5,382,842 indicate that cPLA$_2$ inhibitors are expected to be used to treat inflammatory conditions, such as psoriasis, asthma, and arthritis (see, col. 15), and prophesizes that such anti-inflammatory compounds can be identified as cPLA$_2$ inhibitors.

A number of inhibitors of PLA$_2$ activity have been reported. Bromoenol lactone and trifluoromethyl ketones (e.g., palmitoyl trifluoromethyl ketone, arachidonyl trifluoromethyl ketone) have been reported to be capable of inhibiting a Ca$^{+2}$-independent PLA$_2$ activity (Ackermann et al. (1995) *J. Biol. Chem.* 270: 445) as well as cPLA$_2$ (Street et al. (1993) *Biochemistry* 32: 5935). Several benzenesulfonamide derivatives have also been reported to be capable of inhibiting PLA$_2$ activity (European Patent Application 468 054; Oinuma et al. (1991) *J. Med. Chem.* 34: 2260).

Reynolds et al. (1994) *Anal. Biochem.* 217: 25 describe a convenient microtiter plate assay for cPLA$_2$. Currie et al. (1994) *Biochem. J.* 304: 923, describe a cPLA$_2$ assay for assaying cPLA$_2$ activity from activated whole cells. This assay can be adapted for assay of related PLA$_2$ activity, whether from cPLA$_2$ or other PLA$_2$ enzymes having similar catalytic activities.

A suitable source of cPLA$_2$ can be obtained, if desired, by expression of a recombinant expression vector in a suitable host cell, as described in U.S. Pat. No. 5,354,677, or by conventional biochemical purification from mammalian cells, as is known in the art.

Methods for Identifying Aβ Neurodegeneration Inhibitors

One method to identify active agents which inhibit the development of AD-type neuropathology is simply brute force screening of all possible chemical structures in a suitable cellular and/or animal model of AD. Unfortunately, the complexity and structural potential of chemistry makes a thorough search of all of the chemical structural space impossible, even if facile synthetic methods were available for all potential compounds. Because an exhaustive search of chemical space is not possible, it is exceedingly important to identify properties of likely inhibitors of Aβ-mediated neurodegenerative processes involved in AD and related diseases.

In order to expedite the screening of compound libraries and to increase the probability of obtaining active agents which inhibit neurodegeneration associated with Aβ and/or AD, it is desirable to preselect compounds which are known or suspected inhibitors of PLA$_2$ (based on structural homology to substrates or inhibitors), and preferably are selective inhibitors of cytosolic PLA$_2$. The PLA$_2$ inhibitors are typically identified by initially employing a PLA$_2$ assay, which may comprise an in vitro PLA$_2$ enzyme assay using a standardized amount of a purified or recombinantly produced mammalian PLA$_2$, such as human cPLA$_2$, and/or may comprise a whole cell assay, or a combination thereof. For example and not limitation, a primary PLA$_2$ assay can be performed essentially according to Reynolds et al. (1994) *Anal. Biochem.* 217: 25, with an agent added to test assay reactions and compared to a control reaction lacking an added agent. Agents which are found to inhibit PLA$_2$ activity in the assay are then selected for subsequent testing in a secondary assay. An alternative primary assay can optionally comprise a whole cell PLA$_2$ assay, such as that disclosed in Currie et al. (1994) *Biochem. J.* 304: 923. Other suitable assays for measuring the capacity of an agent to inhibit PLA$_2$ will be apparent to those in the art in view of Applicants' specification; and further in view of U.S. Pat. Nos. 5,354,677 and 5,382,842, incorporated herein by reference. The primary PLA$_2$ assays can also be multiplexed, so that agents which are positively identified in one primary assay are verified as bona fide PLA$_2$ inhibitors in another type of primary assay. Preferably, the PLA$_2$ activity is a cytosolic PLA$_2$ enzyme, most typically a calcium-dependent cPLA$_2$.

Agents selected in the primary assay(s) as PLA$_2$ inhibitors are evaluated for their capacity to inhibit neuronal degeneration and/or microglial and/or astrocyte (astrocytoma cells) and/or monocyte activation in mammalian cortical or hippocampal cell cultures or neuronal cell line cultures, mixed neuronal/glial cultures, or the like, treated with Aβ as described in the Examples, or by other suitable neurotoxicity assays for measuring AD and/or Aβ-mediated neurodegeneration. These secondary assays measure the ability of a selected agent to inhibit neurodegeneration in AD-type disease models. Typically, a secondary assay is performed using a primary rat or human cortical or hippocampal neuron culture and/or a rat or human cortical astrocyte/microglia culture, as described herein; alternatively, a neuronal cell line can be employed, typically with (1) primary glial cells and/or a glial cell line, and/or (2) primary astrocytes and/or an astrocytic cell line (astrocytoma cells). However, other suitable AD models can be employed, such as transgenic mice expressing an APP transgene which results in the development of AD-type neuropathology in the mice. A plurality of secondary assays may also be multiplexed, so that for example agents which score positive as in a neuronal cell culture Aβ-mediated neurodegeneration inhibition assay can be tested in mammalian model of neurodegenerative disease (e.g., a transgenic mouse AD model), and vice versa.

Thus, a primary screening assay to identify $PLA_2$ inhibitors is performed prior to a secondary screening assay to identify Aβ-mediated neurodegeneration inhibitors. An advantage of this approach is that it substantially reduces the chemical structure space which needs to be searched to identify Aβ-mediated neurodegeneration inhibitors. Furthermore, several structural families of $PLA_2$ inhibitors are known, whereas there is no known inhibitor of AD-type neurodegeneration which is substantially effective; thus the agent search can be focused to compounds likely to be $PLA_2$ inhibitors based on their structural homology to identified $PLA_2$ inhibitors or to $PLA_2$ inhibitors prophesized by rational design based on the known $PLA_2$ protein structures, such as human $cPLA_2$.

Agents

A bank or library of agents is selected at the discretion of the practitioner. Typical agents will be structural congeners of known $PLA_2$ inhibitors, or compounds rationally predicted to have $PLA_2$ inhibition activity. In some, embodiments random or pseudorandom agent libraries can be employed, as can combinatorial chemistry libraries, peptide/peptoid libraries, and the like.

In general, agents such as: aminosteroids (e.g., 21-aminosteroids), (e)-6-(bromomethylene)tetrahydro-3-(1-naphthalenyl)-2H-pyran-2-one, or the like, and halogenated methylketones of arachidonic acid or palmitic acid, or the like, can be suitable $PLA_2$ inhibitors. These compounds are are suitable for use as agents, especially to obtain irreversible $PLA_2$ inhibitors which may have an advantageous duration of action. Benzenesulfonamides and various arylsulfonamides are also suitable agents to include in a compound library of the invention. Typically, such compounds are selected from the group of known chemical compounds known in the chemical and pharmaceutical literature; from described compound libraries; from natural compounds which may comprise undetermined structures; and from other suitable sources of chemical diversity.

Essentially any type of agent desired by the practitioner may be evaluated using the method, although agents believed likely to have $PLA_2$ inhibition activity are typically preferred.

Examples of the types of compounds believed to be preferable for inclusion in agent libraries include: BIRM 270 (Farina et al. (1994) *J. Pharmacol Exp. Therap.* 271: 1418; Ro23-9358 (LeMahieu et al. (1993) *J. Med. Chem.* 36: 3029; U73122 (Chen et al. (1995) *Life Sciences* 56: 103); BMS-181162 (Tramposch et al. (1994) *J. Pharmacol. Exp. Therap.* 271: 852; Burke et al. (1995) *J. Biol. Chem.* 270: 274); and "Compound 1" (Abdullah et al. (1995) *Bioorganic and Medicinal Chem. Let.* 5: 519), among others.

Agents which are identified as active agents for $PLA_2$ inhibition and inhibition of Aβ-mediated neurodegeneration are administered to cell populations comprising neuronal cells to reduce or arrest neuronal cell death via $PLA_2$-dependent pathways.

The agents can be any molecule, compound, or other substance which can be added to the cell culture or administered to a test animal without substantially interfering with cell or animal viability. Suitable test agents may be small molecules, biological polymers, such as polypeptides, polysaccharides, polynucleotides, and the like. The test compounds will typically be administered to transgenic animals at a dosage of from 1 ng/kg to 10 mg/kg, usually from 1 µg/kg to 1 mg/kg.

Preferably, active agents are able to cross the blood-brain barrier of a human to produce a therapeutically efficacious concentration in cerebrospinal fluid and CNS tissues (e.g., cortical neurons). Other approaches to enhancing delivery of drugs, particularly across the blood-brain barrier, utilize pharmacologic-based procedures involving drug latentiation or the conversion of hydrophilic drugs into lipid-soluble drugs. The majority of the latentiation approaches involve blocking the hydroxyl, carboxyl and primary amine groups on the drug to make it more lipid-soluble and therefore more easily transported across the blood-brain barrier. Pardridge and Schimmel, U.S. Pat. No. 4,902,505, disclose chimeric peptides for enhancing transport by receptor-mediated transcytosis.

Alzheimer's Disease Model Systems

Generally, the nomenclature used hereafter and the laboratory procedures in cell culture, molecular genetics, and nucleic acid chemistry and hybridization described below are those well known and commonly employed in the art. Standard techniques are used for recombinant nucleic acid methods, polynucleotide synthesis, cell culture, and transgene incorporation (e.g., electroporation, microinjection, lipofection). Generally enzymatic reactions, oligonucleotide synthesis, and purification steps are performed according to the manufacturer's specifications. The techniques and procedures are generally performed according to conventional methods in the art and various general references which are provided throughout this document. The procedures therein are believed to be well known in the art and are provided for the convenience of the reader. All the information contained therein is incorporated herein by reference.

Chimeric targeted mice are derived according to Hogan, et al., *Manipulating the Mouse Embryo: A Laboratory Manual*, Cold Spring Harbor Laboratory (1988) and *Teratocarcinomas and Embryonic Stem Cells: A Practical Approach*, E. J. Robertson, ed., IRL Press, Washington, D.C., (1987) which are incorporated herein by reference.

Embryonic stem cells are manipulated according to published procedures (*Teratocarcinomas and Embryonic Stem Cells: A Practical Approach*, E. J. Robertson, ed., IRL Press, Washington, D.C. (1987); Zjilstra et al., *Nature* 342:435–438 (1989); and Schwartzberg et al., *Science* 246:799–803 (1989), each of which is incorporated herein by reference).

Oligonucleotides can be synthesized on an Applied Bio Systems oligonucleotide synthesizer according to specifications provided by the manufacturer.

In one aspect of the invention are provided nonhuman animals harboring at least one copy of a transgene comprising a polynucleotide sequence which encodes a heterologous $PLA_2$ polypeptide operably linked to a transcription regulatory sequence capable of producing expression of the heterologous $PLA_2$ polypeptide in the transgenic nonhuman animal. Said heterologous $PLA_2$ polypeptide is expressed in cells which normally express the naturally-occurring endogenous $PLA_2$ gene (if present). Typically, the nonhuman animal is a mouse and the heterologous $PLA_2$ gene is a human $PLA_2$ gene, such as the human $cPLA_2$ gene. Such transgenes typically comprise a $PLA_2$ expression cassette, wherein a linked promoter and, preferably, an enhancer drive expression of structural sequences encoding a heterologous $PLA_2$ polypeptide in neuronal cell types. Often, the mouse $cPLA_2$ gene is the inactivated target gene and optionally includes a transgene encoding a human $cPLA_2$ polypeptide having $PLA_2$ activity.

The invention also provides transgenes comprising a gene encoding a human $PLA_2$, said gene operably linked to a transcription regulatory sequence functional in the host transgenic animal (e.g., a neural-specific promoter). Such transgenes are typically integrated into a host chromosomal location by nonhomologous integration. The transgenes may further comprise a selectable marker, such as a neo or gpt gene operably linked to a constitutive promoter, such as a phosphoglycerate kinase (pgk) promoter or HSV tk gene promoter linked to an enhancer (e.g., SV40 enhancer).

The invention further provides nonhuman transgenic animals, typically nonhuman mammals such as mice, which harbor at least one copy of a transgene or targeting construct of the invention, either homologously or nonhomologously integrated into an endogenous chromosomal location so as to encode a human $PLA_2$ polypeptide. Such transgenic animals are usually produced by introducing the transgene or targeting construct into a fertilized egg or embryonic stem (ES) cell, typically by microinjection, electroporation, lipofection, or biolistics. The transgenic animals express the human $PLA_2$ gene of the transgene (or homologously recombined targeting construct), typically in brain tissue. Such animals are suitable for use in a variety of disease model and drug screening uses, for sales to commercial laboratories conducting toxicological evaluation of compounds believed likely of producing chronic neuronal toxicity, as well as other applications.

The invention also provides nonhuman animals and cells which harbor at least one integrated targeting construct that functionally disrupts an endogenous $PLA_2$ gene locus, typically by deleting or mutating a genetic element (e.g., exon sequence, splicing signal, promoter, enhancer) that is required for efficient functional expression of a complete gene product.

The invention also provides transgenic nonhuman animals, such as a non-primate mammal, that have at least one inactivated endogenous $PLA_2$ allele, and preferably are homozygous for inactivated $PLA_2$ alleles, and which are substantially incapable of directing the efficient expression of endogenous (i.e., wildtype) $PLA_2$. For example, in a preferred embodiment, a transgenic mouse is homozygous for inactivated endogenous $PLA_2$ alleles and is substantially incapable of producing murine $PLA_2$ encoded by a endogenous (i.e., naturally-occurring) $PLA_2$ gene. Such a transgenic mouse, having inactivated endogenous $PLA_2$ genes, is a preferred host recipient for a transgene encoding a heterologous $PLA_2$ polypeptide, preferably a human $PLA_2$ polypeptide. For example, human $PLA_2$ may be encoded and expressed from a heterologous transgene(s) in such transgenic mice. Such heterologous transgenes may be integrated in a nonhomologous location in a chromosome of the nonhuman animal, or may be integrated by homologous recombination or gene conversion into a nonhuman $PLA_2$ gene locus, thereby effecting simultaneous knockout of the endogenous $PLA_2$ gene (or segment thereof) and replacement with the human $PLA_2$ gene (or segment thereof). A preferred $PLA_2$ gene is the $cPLA_2$ gene.

Such animals are suitable for use in a variety of disease model and drug screening uses, for sales to commercial laboratories conducting toxicological evaluation of compounds believed likely of producing chronic neuronal toxicity, as well as other applications.

Particular techniques for producing transgenic mice which express the Swedish form of βAPP, APP codon 717 variants, and other AD-associated transgenic disease models are described elsewhere in the art. It will be appreciated that the preparation of other transgenic animals expressing the Swedish human βAPP and/or APP codon 717 mutants may easily be accomplished, including rats, hamsters, guinea pigs, rabbits, and the like. The effect of test compounds on $PLA_2$ activity in βAPP-transgenic test animals may be measured in various specimens from the test animals.

Antisense Polynucleotides

Additional embodiments directed to modulation of $PLA_2$ activity include methods that employ specific antisense polynucleotides complementary to all or part of the human or mouse $PLA_2$ sequences, such as antisense polynucleotides to the human $cPLA_2$ gene or mRNA. Such complementary antisense polynucleotides may include nucleotide substitutions, additions, deletions, or transpositions, so long as specific hybridization to the relevant target sequence corresponding to human or mouse $PLA_2$ cDNA is retained as a functional property of the polynucleotide. Complementary antisense polynucleotides include soluble antisense RNA or DNA oligonucleotides which can hybridize specifically to $PLA_2$ mRNA species and prevent transcription of the mRNA species and/or translation of the encoded polypeptide (Ching et al. (1989) *Proc. Natl. Acad. Sci. U.S.A.* 86: 10006; Broder et al. (1990) *Ann. Int. Med.* 113: 604; Loreau et al. (1990) *FEBS Letters* 274: 53; Holcenberg et al., WO91/11535; U.S. Ser. No. 07/530,165; WO91/09865; WO91/04753; WO90/13641; and EP 386563, each of which is incorporated herein by reference). The antisense polynucleotides therefore inhibit production of $PLA_2$ polypeptides. Since $PLA_2$ protein expression is associated with activation and enzymatic activity, antisense polynucleotides that prevent transcription and/or translation of mRNA corresponding to $PLA_2$ polypeptides may inhibit $PLA_2$ activity and/or reverse the activated phenotype of Aβ-stimulated neuronal and/or microglial cells and/or astrocytic cells and/or monocytic cells. Compositions containing a therapeutically effective dosage of $PLA_2$ antisense polynucleotides may be administered for treatment of Aβ-mediated neurodegenerative diseases, and for inhibition of Alzheimer's Disease and Down's Syndrome, if desired. Antisense polynucleotides of various lengths may be produced, although such antisense polynucleotides typically comprise a sequence of about at least 25 consecutive nucleotides which are substantially identical to a naturally-occurring $PLA_2$ polynucleotide sequence, and typically which are identical to a human $PLA_2$ sequence, such as human $cPLA_2$.

Antisense polynucleotides may be produced from a heterologous expression cassette in a transfectant cell or transgenic cell. Alternatively, the antisense polynucleotides may comprise soluble oligonucleotides that are administered to the external milieu, either in the culture medium in vitro or in the cerebrospinal fluid or direct brain application in vivo. Soluble antisense polynucleotides present in the external milieu have been shown to gain access to the cytoplasm and inhibit translation of specific mRNA species. In some embodiments the antisense polynucleotides comprise methylphosphonate moieties or are polyamide nucleic acids (PNAs). For general methods relating to antisense polynucleotides, see *Antisense RNA and DNA*, (1988), D. A. Melton, Ed., Cold Spring Harbor Laboratory, Cold Spring Harbor, N.Y.).

Compositions of Neurodegeneration Inhibitors

Active agents which are $PLA_2$ inhibitors and also inhibit neuronal degeneration in AD-type disease models can be used to retard or reduced AD-type neuropathology in vivo. Thus, the present invention further comprises pharmaceutical compositions incorporating a compound selected by the above-described method and including in a pharmaceutically acceptable carrier. Such pharmaceutical compositions should contain a therapeutic or prophylactic amount of at least one compound identified by the method of the present invention. The pharmaceutically acceptable carrier can be any compatible, non-toxic substance suitable to deliver the compounds to an intended host. Sterile water, alcohol, fats, waxes, and inert solids may be used as the carrier. Pharmaceutically acceptable adjuvants, buffering agents, dispersing agents, and the like may also be incorporated into the pharmaceutical compositions. Preparation of pharmaceutical conditions incorporating active agents is well described in the medical and scientific literature. See, for example, Remington's Pharmaceutical Sciences, Mack Publishing Company, Easton, Pa., 16th Ed., 1982, the disclosure of which is incorporated herein by reference.

The pharmaceutical compositions just described are suitable for systemic administration to the host, including both parenteral, topical, and oral administration, including intracranial administration. Thus, the present invention provides compositions for administration to a host, where the compositions comprise a pharmaceutically acceptable solution of the identified $PLA_2$-inhibitory compound in an acceptable carrier, as described above. Such formulations can be used therapeutically on mammals having AD-type neuropathology or disease progression of a related neurodegenerative disease.

Compositions containing the present $PLA_2$ inhibitors can be administered for prophylactic and/or therapeutic treatments of neurodegenerative disease. In therapeutic application, compositions are administered to a patient already affected by the particular neurodegenerative disease, in an amount sufficient to cure or at least partially arrest the condition and its complications. An amount adequate to accomplish this is defined as a "therapeutically effective dose" or "efficacious dose." Amounts effective for this use will depend upon the severity of the condition, the general state of the patient, and the route of administration, but generally range from about 1 mg to about 10 g of $PLA_2$ inhibitor per dose, with dosages of from 10 mg to 2000 mg per patient being more commonly used. Suitable concentrations (i.e., efficacious dose) can be determined by various methods, including generating an empirical dose-response curve, predicting potency and efficacy of a congener by using QSAR methods or molecular modeling, and other methods used in the pharmaceutical sciences.

The invention also provides the use of a $PLA_2$ inhibitor to slow, arrest, or reverse the development of a neurodegenerative disease such as Alzheimer's disease or Down's Syndrome in a human patient; an efficacious amount of the $PLA_2$ inhibitor is administered to the patient to inhibit progression of the disease.

The following examples are provided for illustration and are not intended to limit the invention to the specific example provided.

EXPERIMENTAL EXAMPLES

General Methods

Pathogenic Aβ peptide: The following Aβ peptides were synthesized and used, typically after being dissolved in water. The Aβ peptides typically aggregate and/or change the folding state of the peptide over time into conformations having varying pathogenicity/neurotoxicity. Each batch of Aβ peptide stock solution is checked for toxicity on neuronal cell cultures or mixed neuronal/glial cell cultures, according to methods described herein and methods known to those skilled in the art.

Aβ1–40, amino acid sequence (SEQ ID NO:2)=

DAEFRHDSGYEVHHQKLVFFAEDVGSNKGAIIGLMVGGVV (SEQ ID NO:2)

Aβ1–42, amino acid sequence (SEQ ID NO:1)=

DAEFRHDSGYEVHHQKLVFFAEDVGSNK-GAIIGLMVGGVVIA (SEQ ID NO:1)

Primary Rat Cortical or Hippocampal Neurons

Cultures of rat cortical neurons were established from 18 day rat fetuses. Cortical tissue or hippocampal tissue was dissociated by incubation in a trypsin/EDTA solution (0.05% trypsin +0.53 mM EDTA in HBSS; Gibco) for 20 minutes at 37° C. The trypsin was then inactivated by resuspending the cells in serum-containing medium (DMEM/FBS): Dulbecco's Modified Eagle's Medium (DMEM) containing 4.5 g/L glucose, 1 mM sodium pyruvate, 1 mM glutamine, 100 Units/ml penicillin, 100 µg/ml streptomycin, and supplemented with 10% heat-inactivated fetal bovine serum (Gibco). Cells were then pelleted by centrifugation and resuspended in a chemically-defined medium (DMEM/B27): DMEM containing B27 supplement (Gibco) in place of FBS. Polyethyleneimine (PEI)-coated 6.4-mm (96-well) dishes were rinsed once with DMEM/FBS, and then seeded at $0.75–1.25 \times 10^5$ cells per well in 0.1 ml DMEM/B27. Cultures were maintained in a $H_2O$ )-saturated incubator with an atmosphere of 90% air/10% $CO_2$ at 37° C. Cell viability was visually assessed by phase contrast microscopy and quantified by measuring the reduction of alamarBlue™ (Alamar Biosciences, Inc.) as described below. Serum replacement with B27 supplement yields nearly pure neuronal cultures as judged by immunocytochemistry for glial fibrillary acidic protein and neuron-specific enolase (Brewer et al. (1993), *J. Neurosci. Res.* 35(5):567–576.

Primary Human Cortical or Hippocampal Neurons

Cultures of human cortical or hippocampal neurons were prepared using a modification of the procedure described in P. Seubert et al. (1992), *Nature* 359:325–327. Cortical or hippocampal tissue was dissociated by incubation in a trypsin/EDTA solution (0.05% trypsin +0.53 mM EDTA in HBSS; Gibco) for 20 minutes at 37° C. The trypsin was then inactivated by resuspending the cells in serum-containing medium (MEM/FBS): Modified Eagle's Medium (MEM)

containing 1% glucose, 1 mM sodium pyruvate, 1 mM glutamine, and supplemented with 10% fetal bovine serum (Gibco). Cells were then pelleted by centrifugation and resuspended in a chemically-defined medium (MEM/B27): MEM containing B27 supplement (Gibco) in place of FBS. Polyethyleneimine (PEI)-coated 6.4-mm (96-well) dishes were rinsed once with MEM/FBS, and then seeded at $0.75-1.25 \times 10^5$ cells per well in 0.1 ml MEM/B27. Cultures were maintained in a $H_2O$-saturated incubator with an atmosphere of 95% air/5% $CO_2$ at 37° C. The culture medium was exchanged twice weekly.

Primary Human Cortical or Hippocampal Astrocytes and Microglia

Cultures of human cortical or hippocampal astrocytes and microglia were prepared using a modification of the procedure described for cortical neurons. Cortical tissue from fetuses of 16 to 20 weeks of gestation was washed 3 times in $Ca^{2+}/Mg^{2+}$free Hanks balanced salt solution (CMF HBSS) and then dissociated by repeated pipetting. The solution was brought to a final volume of 80 ml CMF HBSS for approximately 10 ml of tissue. DNase (Sigma) was added to a final concentration of 0.05 mg/ml. 20 ml of the solution was passed through one 100 μm nylon cell strained (Falcon). The cells were then centrifuged for 5 minutes at 200×G in an IEC Clinical Centrifuge and resuspended in a trypsin/EDTA solution (0.05% trypsin+0.53 mM EDTA in HBSS; Gibco) and incubated for 20 minutes at 37°C. (10 ml of trypsin was added per 2–3 ml of tissue). The trypsin was then inactivated by adding (MEM/FBS): Modified Eagle's Medium (MEM) containing 1% glucose, 1 mM sodium pyruvate, 1 mM glutamine, and supplemented with 10% fetal bovine serum (JRH). After adding a final concentration of 0.05 mg/ml DNase the cells were resuspended and then pelleted by centrifugation and resuspended in MEM/FBS. $1.6 \times 10^8$ cells were seeded in a T-150 tissue culture flask coated with polyethyleneimine (PEI). (10% PEI (Sigma) was diluted 1:10 in $H_2O$, filtered through a 45 mm unit and then diluted into 150 mM sodium borate pH 8.5 at 1:100. The flasks were coated overnight at room temperature, washed two times in PBS and coated with 20 ml/flask of MEM/FBS at 37° C. for at least one hour prior to plating cells.) Cultures were maintained in a $H_2O$-saturated incubator with an atmosphere of 95% air/5% $CO_2$ at 37° C. The culture medium was changed one and four days after plating and the cultures were then left undisturbed for at least one week. After approximately two weeks in vitro, the flasks were gently shaken and floating microglia were collected and centrifuged for 5 minutes at 200×G in an IEC Clinical Centrifuge. The microglia were reseeded in 96 well tissue culture plates at a density of 5,000–40,000 cells/well in 125 μl in MEM/FBS. Astrocyte cultures were prepared by multiple passaging of the established mixed brain cell cultures. Each T-150 was incubated for 3–4 minutes at 37°C. with a trypsin/EDTA solution (see above). The trypsin was then inactivated by adding MEM/FBS. The cells were triturated and then pelleted by centrifugation and resuspended in MEM/FBS. The cells from one T-150 were seeded at a 1:30 to 1:5 dilution in T-150's not coated. Just prior to confluency the cells were repassaged by trypsinization as described above. This process was repeated until the cultures were >98% pure astrocytes.

Experimental treatments and analysis of neuronal survival

Amyloid-β (Aβ) stock solutions were prepared as 1 mM stocks in sterile dd$H_2O$ immediately prior to addition to cultures. Rat cortical neurons were exposed to Aβ by removing the culture medium and replacing it with DMEM/N2 or DMEM/B27 containing Aβ1–40. Human cortical neurons were exposed to Aβ by removing the culture medium and replacing it with MEM, MEM/N2, or MEM/B27 containing Aβ1–40. Cultures were maintained for 2–4 days before neuronal survival was quantified using alamarBlue™.

Neurotoxicity Assay using alamarBlue™

The alamarBlue™ assay incorporated a proprietary fluorometric/colorimetric metabolic indicator (Alamar Biosciences, Inc.). Viable cells convert alamarBlue™ from an oxidized (non-fluorescent, blue) form to a reduced (fluorescent, red) form. Assays were performed by replacing the culture media with a 10% alamarBlue™ solution in DMEM (rat cortical cultures) or MEM (human cortical cultures). Reduction of alamarBlue™ was determined spectrofluorometrically using a Millipore Cytofluor 2350 Scanner (excitation, 560 mM; emission, 590 nm) and CytoCalc™ software (Millipore Corporation). Neuronal viability as assessed by alamarBlue™ was comparable to that obtained by measuring the fluorogenic probe calcein AM, the release of the cytoplasmic enzyme lactate dehydrogenase (LDH), or the reduction of the tetrazolium salt, 2,3-bis (2-methoxy-4-nitro-5-sulfophenyl)-2H-tetrazolium-5-carboxanilide (XTT).

Assays of phospholipase $A_2$ activity

Arachidonic acid release assay: Neurons, astrocytes, or microglia are labelled overnight with $^3$H-arachidonic acid. Cultures wells are rinsed several times with medium containing fatty acid free serum albumin and then treated with an activator of phospholipase $A_2$. Released $^3$H-arachidonic acid is measured after various time-points. The amount of cell associated or released free $^3$H-arachidonic acid is an indirect measurement of the activity of phospholipase $A_2$ to cleave arachidonic acid from the sn-2 position of membrane phospholipids. Fatty acid free serum albumin serves as a trap for released $^3$H-arachidonic acid.

Cytosolic phospholipase $A_2$ activity can be determined indirectly by measuring phospholipase $A_2$-mediated release of eicosanoids (prostaglandins, thromboxanes, oxygenated metabolites of arachidonic acid, and leukotrienes) [e.g., Currie et al., Biochem. Journal (1994) 304: 923], platelet activating factor, or lysophosphatidic acid. Cytosolic phospholipase $A_2$ activity can also be measured indirectly by measuring the extent of c$PLA_2$ phosphorylation [Lin et al. (1993), Cell 72:269–78.

EXAMPLE 1: Aβ Induces Cytokine Release in Microglia

Figure 1B:
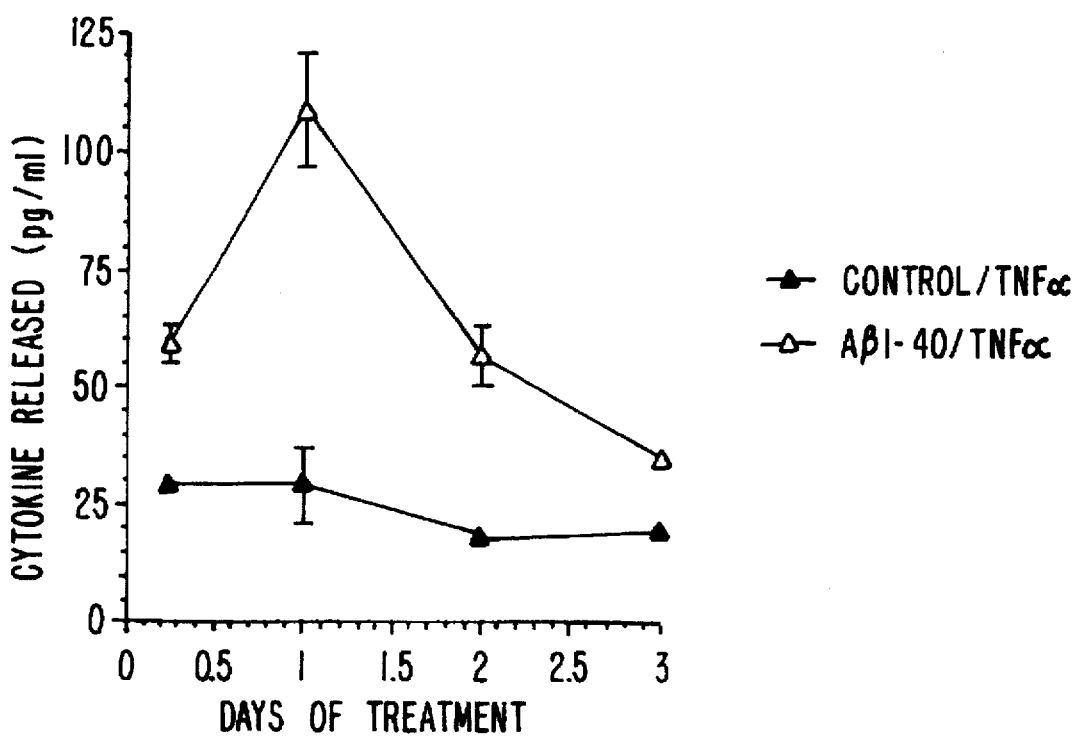
Figure 2A:
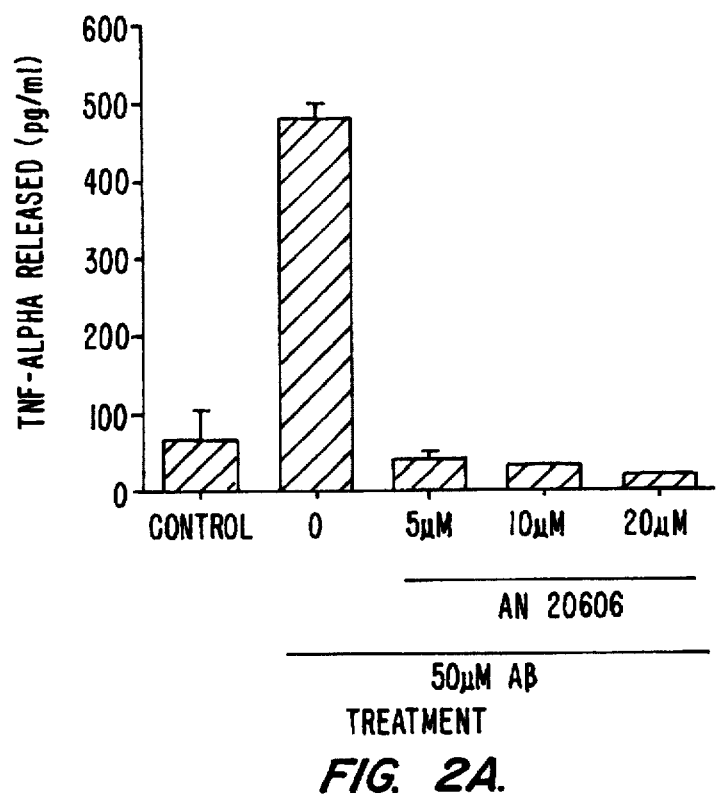
FIG. 2 (panels A-D) shows ELISA results for TNF$\alpha$ or IL-1$\beta$ released from $A\beta$-stimulated microglial cells treated with AN 20606 or AN 20628.
Figure 2B:
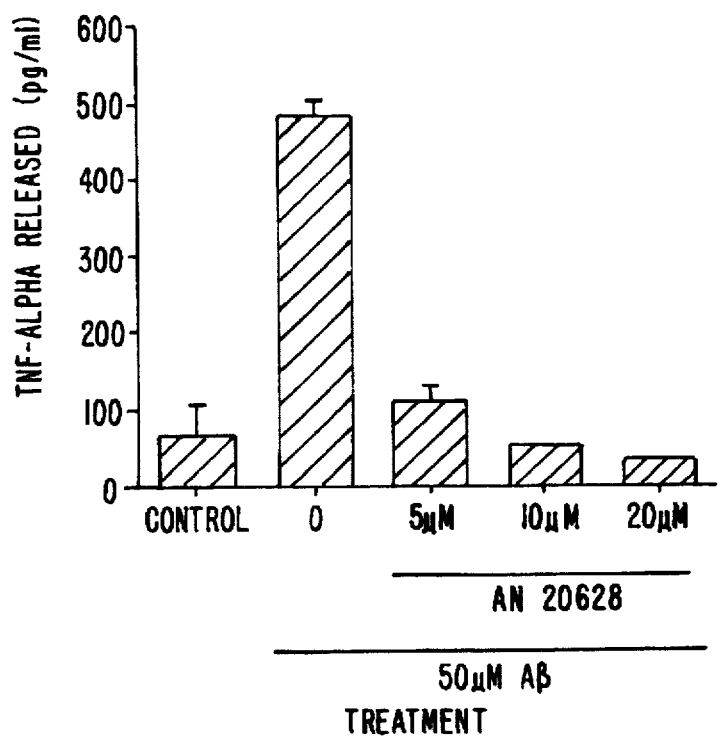
Figure 2C:
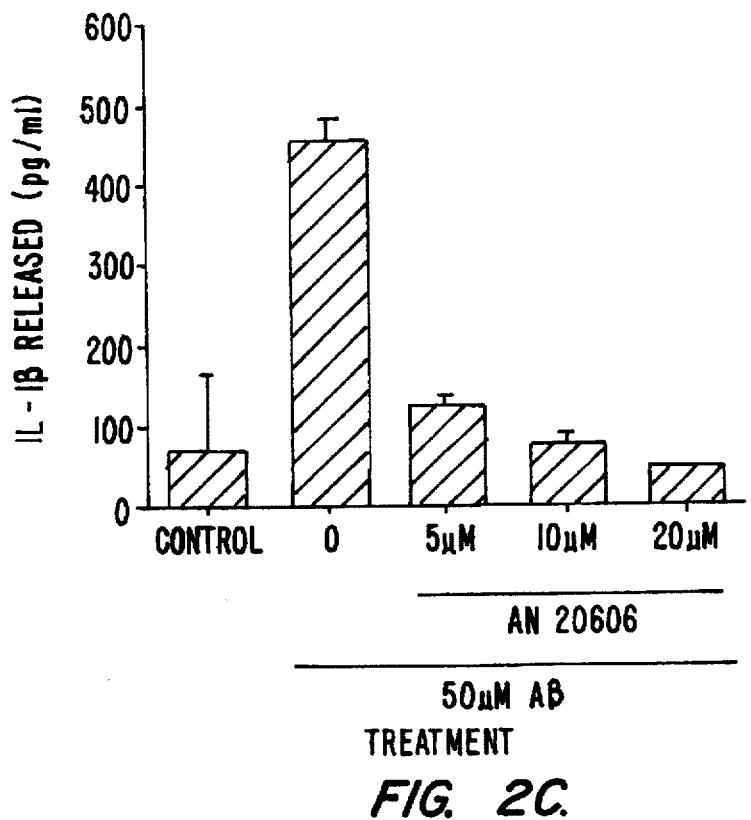
Figure 2D:
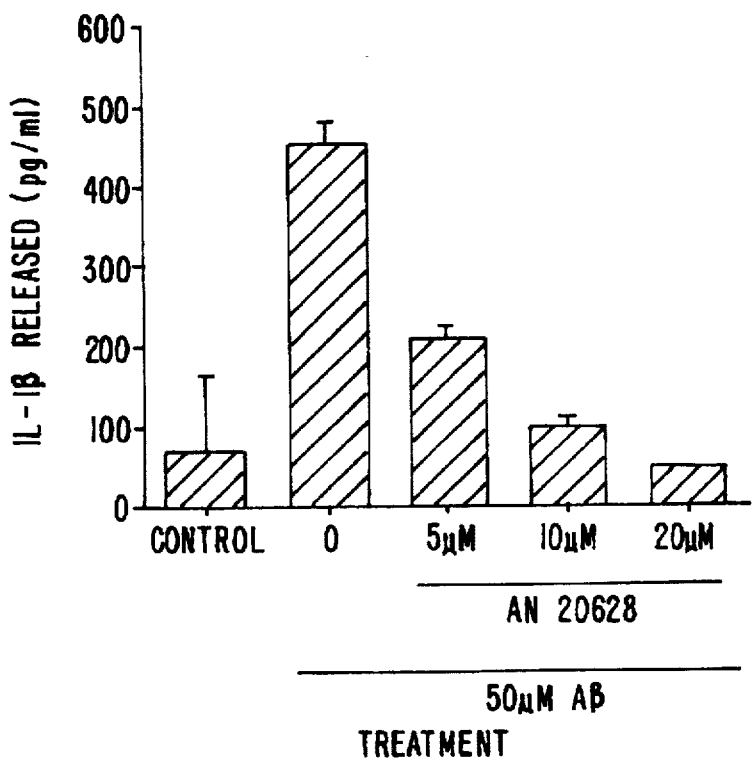

Cultured microglial cells were treated with 50 μM of Aβ1–40 or vehicle only (Control). The levels of IL-1β, IL-6, and TNF-α released into the culture medium were determined by ELISA assay (R&D Systems) according to manufacturer's instructions. FIG. 1 shows the results, indicating that Aβ1–40 stimulates release of IL-1β, IL-6, and TNF-α.

EXAMPLE 2: Benzenesulfonamide Effect on Microglia

The effect of two benzenesulfonamide inhibitors of $PLA_2$ (European Patent Application 468 054) were examined on the activation of microglial cells by Aβ1–40 as in Example 1. N-cycloheptyl-4-[N-methyl-N-[(E)-3-(4-methylsulfonylphenyl)-2-propenoyl]amino]benzenesulfonamide (AN20606) and N-cyclohepyl-4-[N-methyl-N[(E)-3-(4-cyanophenyl-2-propenoyl]amino]benzenesulfonamide (AN 20628) at levels of 0 μM, 5 μM, 10 μM, and 20 μM were added to microglial cultures that had been stimulated with 50μM Aβ1–40 for one day; control cultures were not stimulated with Aβ1–40. The amount of TNF-α and IL-1β released into the culture medium was measured by ELISA. FIG. 2 shows the results graphically. Both PLA$_2$-inhibitory compounds resulted in a marked and dose-dependent decrease in the amount of IL-1β and TNF-α released into the medium as a consequence of Aβ1–40 treatment, indicating that these PLA$_2$-inhibitors also inhibit the induction of cytokine secretion by microglial cells exposed to Aβ.

Selectivity of Aβ Toxicity

The effects of the benzenesulfonamide PLA$_2$ inhibitor AN20606 and the selective cytosolic PLA$_2$ inhibitor arachidonyl trifluoromethyl ketone (AN20579) were examined in cultured human cortical microglia for their selectivity for inhibiting microglia activation mediated by amyloid-β peptide and lipopolysaccharides (LPS). LPS are a major constituent of the cell wall of gama-negative bacteria and are extensively used for generating inflammatory responses in cultured cells and in vivo. As show in Table 3, AN20606 and AN20576 selectively inhibited Aβ1–40-mediated IL-1β and TNFα release. LPS-mediated cytokine release was actually enhanced in the presence of AN20606 and AN20579. The results are shown in Table 1.

This data indicates that PLA$_2$ inhibitors are not general anti-inflammatory agents in human microglia, but are selective inhibitors of Aβ-mediated inflammation.

TABLE 1

| Treatment | IL-1 Released (pg/ml) | TNF Released (pg/ml) |
|---|---|---|
| Control | ND | ND |
| 50 μM Aβ1–40 | 273 ± 65.5 | 105 ± 41 |
| 50 μM Aβ1–40 + 20 μM AN20606 | 16.5 ± 6 (6%) | 3.7 ± 1.4 (4%) |
| 50 μM Aβ1–40 + 20 μM AACOCF3 | 36 ± 7.2 (13%) | 54.8 ± 9.4 (52%) |
| Control | ND | ND |
| 10 ng/ml LPS | 22.7 ± 5.2 | 488 ± 4 |
| 10 ng/ml LPS + 20 μM AN20606 | 37 ± 0.3 (163%) | 632 ± 211 (130%) |
| 10 ng/ml LPS + 20 μM AACOCF3 | 51 ± 6.4 (225%) | 785 ± 50 (161%) |

EXAMPLE 4: Dose-Dependence of Benzenesulfonamide Activity

The effect of the two benzenesulfonamide inhibitors of PLA$_2$ in Example 2 were examined to determine the dose-dependence of their effect on neuronal survival in human cortical neuron cultures exposed to 0 μM, 25μM, or 50 μM of Aβ1–40 and varying doses of the benzenesulfonamide.

Figure 3:
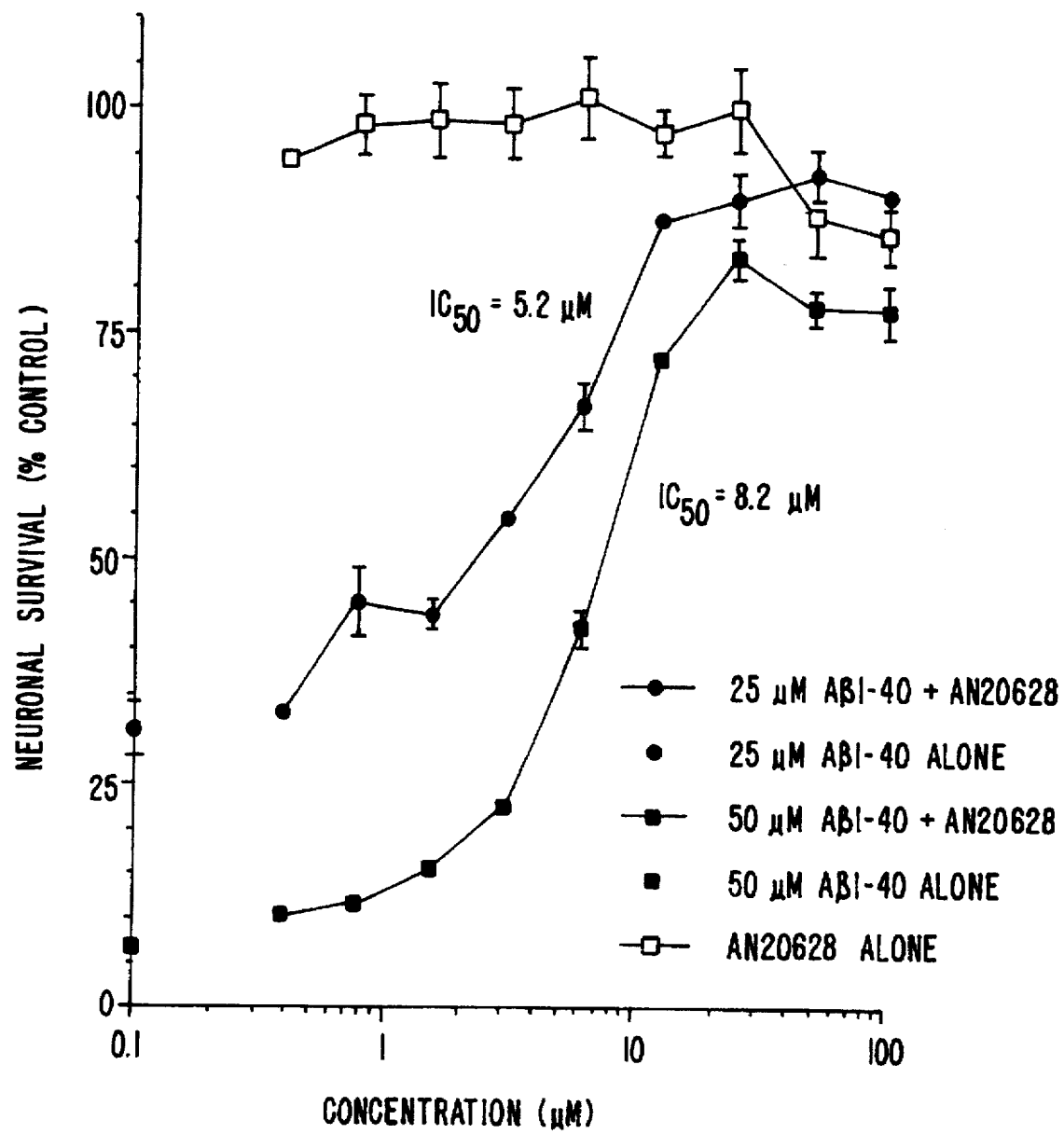
FIG. 3 shows survival curves for neuronal cultures exposed to $A\beta$ peptide and varying concentrations of AN 20628 for three days.
Figure 4:
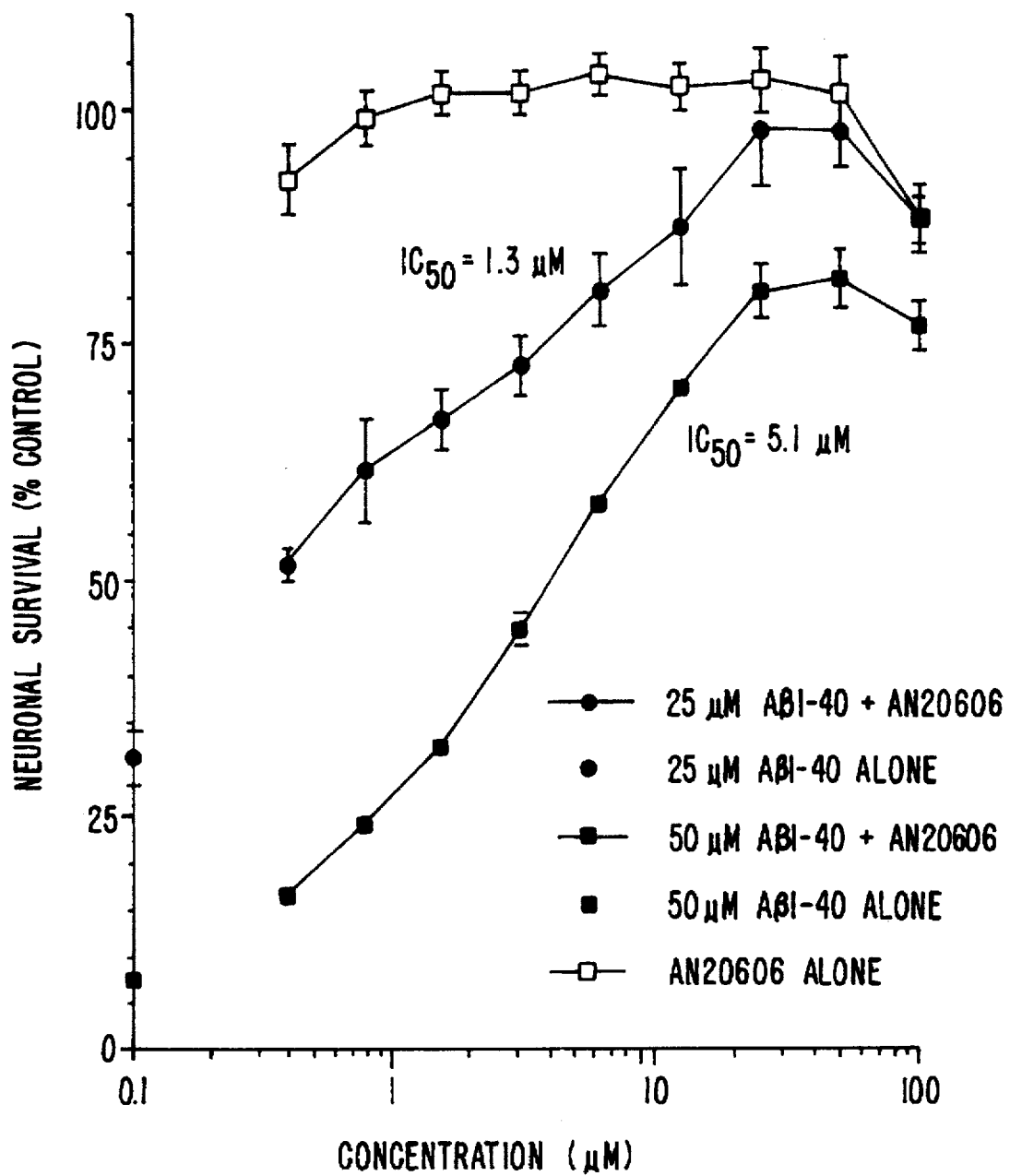
FIG. 4 shows survival curves for neuronal cultures exposed to $A\beta$ peptide and varying concentrations of AN 20628 for three days.

FIG. 3 shows that N-cyclohepyl-4-[N-methyl-N[(E)-3-(4-cyanophenyl0-2-propenoyl]amino] benzenesulfonamide (AN 20628) produces a dose-dependent increase in neuronal survival in the presence of pathogenic Aβ peptide. FIG. 4 shows that N-cycloheptyl-4-[N-methyl-N-[(E)-3-(4-methylsulfonylphenyl)-2-propenoyl]amino] benzenesulfonamide (AN20606) also produces a dose-dependent increase in neuronal survival in the presence of pathogenic Aβ peptide. This demonstrates that two PLA$_2$ inhibitors reduce neuronal toxicity associated with Aβ in a dose-dependent relationship.

EXAMPLE 5: Specificity of Action for PLA$_2$ Inhibition

Figure 5:
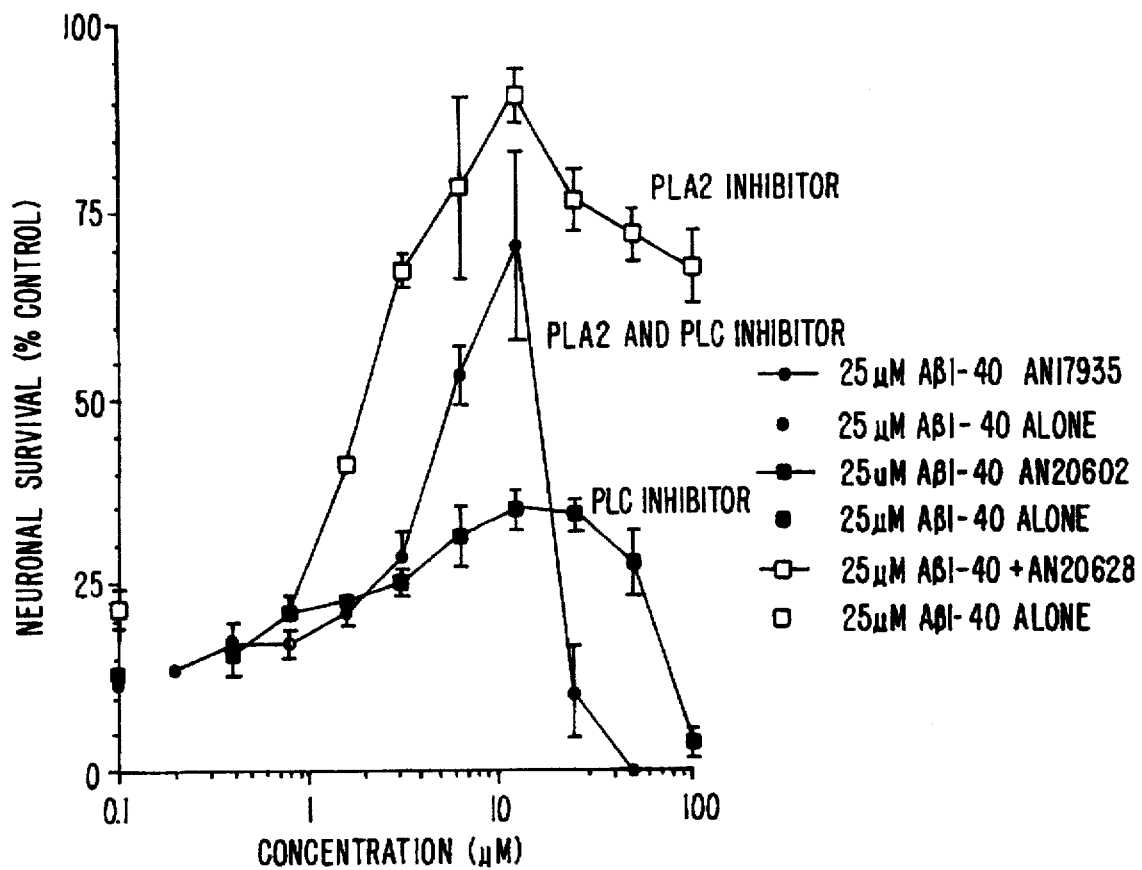
FIG. 5 shows survival curves for neuronal cultures exposed to $A\beta$ peptide and varying concentrations of AN 20628, AN20602, or U 73122 for three days.

To determine the specificity of action of the benzenesulfonamide PLA$_2$ inhibitor as resulting from selective inhibition of PLA$_2$, we compared the effect of two other phospholipase inhibitors: 1-[6-[[(17β)-3-methoxyestra-1,3,5(10)-trien-17-yl]amino]hexyl]-1H-pyrrole-2,5-dione (Chen et al. (1995) Life Sciences 56; 103 [U73122]), which inhibits both PLA$_2$ and PLC (phosphatidyl cholinephospholipase C) and potassium 8(9)-tricyclo[5.2.1.0$^{2,6}$] decyl xanthate (AN20602 or AN20609), which is a PLC inhibitor. FIG. 5 graphically shows the dose-dependent effect of each of these phospholipase inhibitors on survival of neurons in human cortical neuron cultures exposed to Aβ1–40. As is shown in FIG. 5, the effect on enhancing neuronal survival is consistent with specific inhibition of PLA$_2$ activity, and inhibition of PLC is relatively ineffective in enhancing neuronal survival after exposure to Aβ.

EXAMPLE 6: Pretreatment with PLA$_2$ Inhibitors

Figure 6:
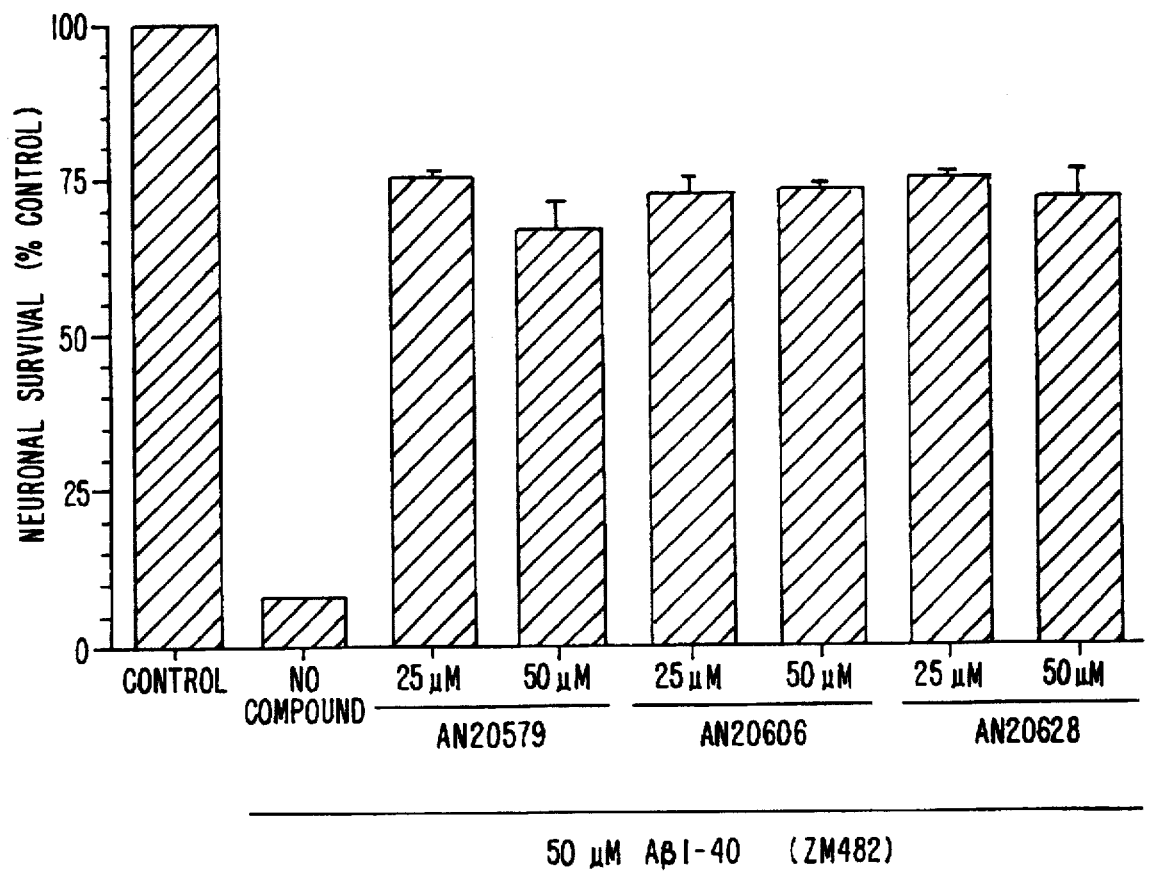
FIG. 6 shows survival of cultured human cortical neurons pretreated with AN 20579, AN 20606, or AN 20628 for two hours prior to exposing the neuronal cells to a pathogenic concentration of $A\beta$ peptide for three days.

The effect of pretreating human cortical neuron cultures with the benzenesulfonamide PLA$_2$ inhibitors and arachidonyl trifluoromethyl ketone prior to exposure to a neurotoxic concentration of Aβ1–40 was determined. FIG. 6 shows that pretreatment with any of the three PLA$_2$ inhibitors produced substantially decreased neuronal death resulting from Aβ1–40 exposure.

Figure 7A:
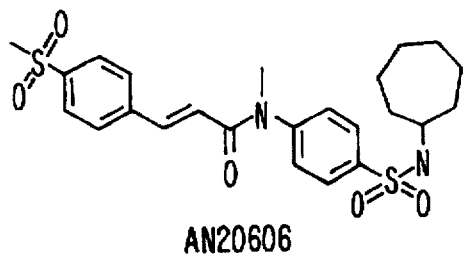
FIG. 7A and 7B shows the structural formulae of compounds used in Examples 1-7.
Figure 7A:
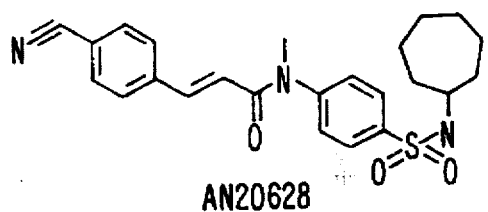
Figure 7A:
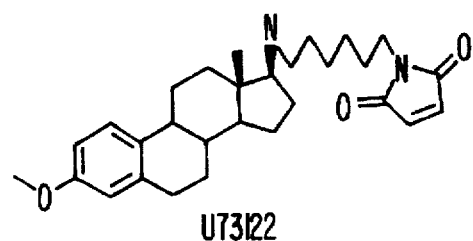
Figure 7A:
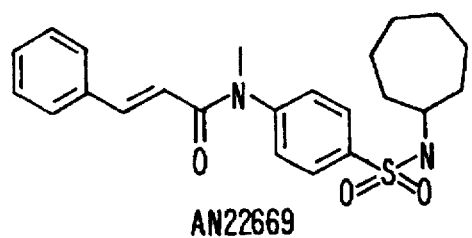
Figure 7A:
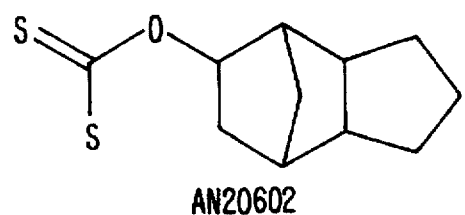
Figure 7A:
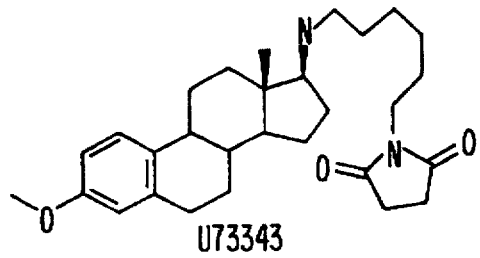
Figure 7A:
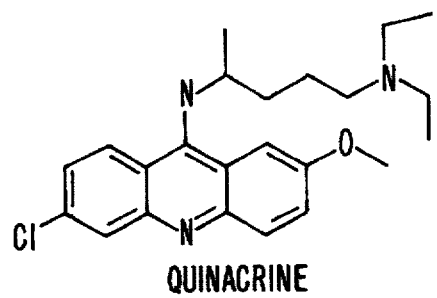
Figure 7B:
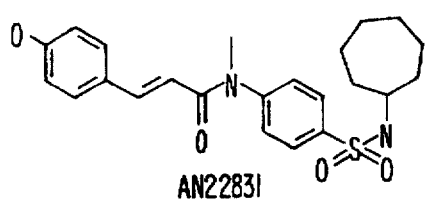
Figure 7B:
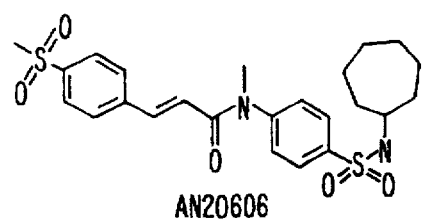
Figure 7B:
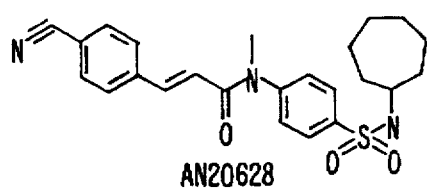
Figure 7B:
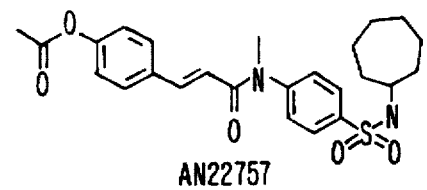
Figure 7B:
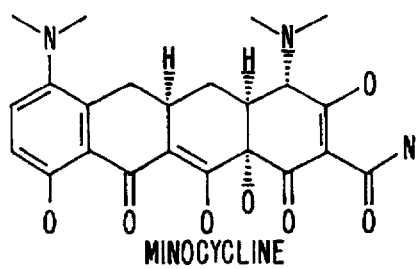
Figure 7B:
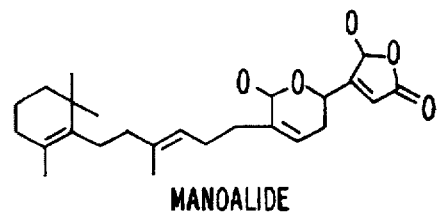
Figure 7B:
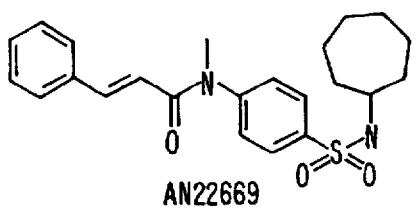
Figure 7B:
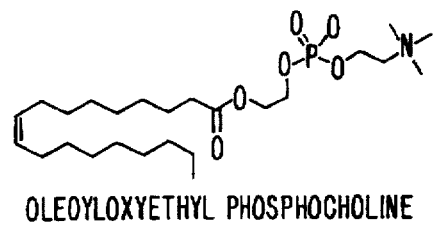
Figure 7B:
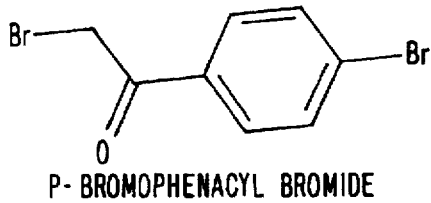
Figure 7B:
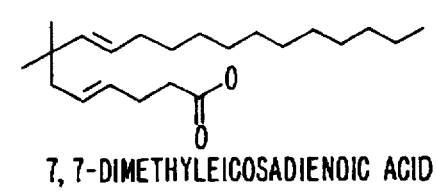
Figure 7B:
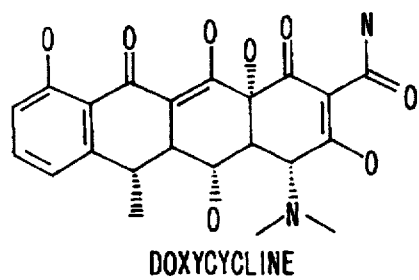
Figure 7B:
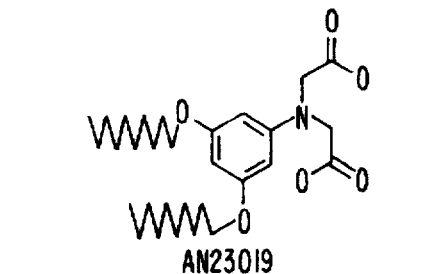

Example 7: Effect of Various PLA2 or PLC Inhibitors on Aβ Neurotoxicity in Human Cortical Neurons Human cortical neurons were treated with 50 μM Aβ1–40 and various inhibitors of PLA$_2$ or PLC. Compounds were added at the time of Aβ1–40 treatment at concentrations 390 nM to 100 μM. Compounds were also added to neuronal cultures in the absence of Aβ1–40. Neuronal survival was determined after 3 days of treatment by alamarBlue®. IC50 is the dose of compound that inhibited Aβ-mediated neurotoxicity by 50%. TD10 and TD50 are the concentrations of compound that resulted in 10% and 50% loss of neuronal survival, respectively, when compound was added to neuronal cultures for 3 days in the absence of Aβ1–40. Data represents the mean ± SD (n=3). ND, not detected at the concentration range used. Results are shown in Table 2. Compound structures are shown in FIGS. 7A and 7B.

TABLE 2

| Compound Name | IC50 (μM) | Max Inh (%) | TD10 (μM) | TD50 (μM) |
|---|---|---|---|---|
| AN20606 | 5 | 80 | 98 | ND |
| AN20628 | 8 | 82 | 73 | ND |
| U73122 | 9 | 66 | 11 | 16 |
| AN22669 | ND | 25 | 26 | ND |
| AN20602 | ND | 25 | 13 | 35 |
| U73343 | ND | 10 | 6 | 8 |
| Quinacrine | ND | 2 | 6 | 9 |

Pretreatment with Inhibitor

Human cortical neurons were treated with 50 μM Aβ1–40 and various inhibitors of PLA$_2$. Compounds were added 2 hours prior to Aβ1–40 treatment at concentrations of 390 nM to 100 μM, and were then re-added at the time of Aβ1–40 treatment. Compounds were also added in an identical manner to neuronal cultures in the absence of Aβ1–40. Neuronal survival was determined after 3 days of treatment by alamarBlue®. IC50 is the dose of compound that inhibited Aβ-mediated neurotoxicity by 50%. TD10 and TD50 are the concentrations of compound that resulted in 10% and 50% loss of neuronal survival, respectively, when compound was added to neuronal cultures for 3 days in the absence of Aβ1–40. Data represents the mean ± SD (n=3). ND, not detected at the concentration range used. The results are shown in Table 3. Compound structures are shown in FIGS. 7A and 7B.

TABLE 3

| Compound Name | IC50 (μM) | Max Inh (%) | TD10 (μM) | TD50 (μM) |
|---|---|---|---|---|
| AN22831 | 2 | 90 | 12 | ND |
| AN20606 | 3 | 89 | 77 | ND |
| AN20628 | 4 | 87 | 50 | ND |
| AN22757 | 4 | 97 | 15 | 25 |
| Minocycline | 71 | 69 | 78 | ND |
| Manoalide | ND | 49 | 8 | 10 |
| AN22669 | ND | 45 | 19 | ND |
| AN23019 | ND | 45 | 71 | ND |
| Bromoenol Lactone | ND | 41 | 6 | 10 |
| Oleoyloxyethyl Phosphocholine | ND | 40 | 17 | 29 |
| p-Bromophenacyl Bromide | ND | 39 | 8 | 10 |
| DEDA | ND | 19 | 100 | ND |
| Doxycycline | ND | 0 | 50 | ND |

Summary of Experimental Examples

The Experimental Examples are indicative that agents which selectively inhibit $PLA_2$ activity protect human neurons from toxicity resulting from exposure to pathogenic Aβ peptide.

Although the present invention has been described in some detail by way of illustration for purposes of clarity of understanding, it will be apparent that certain changes and modifications may be practiced within the scope of the claims.

---

We claim:

1. A method for identifying active agents which inhibit neuronal degeneration induced by Aβ peptide, comprising
   administering an agent to a cell population consisting essentially of neurons or cells from neuronal cell lines, wherein said cell population is exposed to an amount of pathogenic amyloid β("Aβ") peptide that induces neuronal degeneration in the cell population,
   determining whether the agent produces a detectable reduction in the amount and/or rate of neuronal degeneration in the cell population; and
   determining whether the agent produces inhibition of phospholipase A2 "PLA$_2$" activity;
   whereby if the agent produces inhibition of PLA$_2$ activity and inhibits neuronal degeneration, the agent is thereby identified as an active agent.

2. The method according to claim 1, wherein determining whether the agent produces inhibition of PLA$_2$ activity is performed by in vitro assay using a predetermined quantity of PLA$_2$ enzyme.

3. The method according to claim 2, wherein the PLA$_2$ is produced by expression of a recombinant expression vector encoding human cytoplasmic phospholipase A2 "cPLA$_2$" in a host cell.

4. The method according to claim 1, wherein the cell population consists essentially of neurons or cells from neuronal cell lines of human or rodent origin.

5. The method of claim 1, wherein the pathogenic amyloid β peptide comprises an amyloid β peptide having amino acids 25–35 of Aβ1–40 (SEQ ID NO:2).

6. The method of claim 5, wherein the pathogenic amyloid β peptide is Aβ1–40 (SEQ ID NO:2) or Aβ1–42 (SEQ ID NO:1).

7. The method of claim 1, wherein determining whether the agent produces inhibition of PLA$_2$ activity comprises determining whether the presence of said agent produces inhibition of cPLA$_2$ activity.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 42 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:1:

```
Asp Ala Glu Phe Arg His Asp Ser Gly Tyr Glu Val His His Gln Lys
 1               5                  10                  15
Leu Val Phe Phe Ala Glu Asp Val Gly Ser Asn Lys Gly Ala Ile Ile
                20                  25                  30
Gly Leu Met Val Gly Gly Val Val Ile Ala
                35              40
```

( 2 ) INFORMATION FOR SEQ ID NO:2:

( i ) SEQUENCE CHARACTERISTICS:
        ( A ) LENGTH: 40 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:2:

```
Asp Ala Glu Phe Arg His Asp Ser Gly Tyr Glu Val His His Gln Lys
 1               5                  10                  15
Leu Val Phe Phe Ala Glu Asp Val Gly Ser Asn Lys Gly Ala Ile Ile
                20                  25                  30
Gly Leu Met Val Gly Gly Val Val
                35              40
```